（12）United States Patent
Datta et al.

(10) Patent No.: US 7,470,786 B2
(45) Date of Patent: Dec. 30, 2008

(54) METHOD FOR MANUFACTURE OF CEFTRIAXONE SODIUM

(75) Inventors: Debashish Datta, Maharashtra (IN); Muralikrishna Dantu, Madhya Pradesh (IN); Pollepeddi Lakshmi Narayana Sharma, Madhya Pradesh (IN); Brijkishore Mishra, Madhya Pradesh (IN)

(73) Assignee: Lupin Limited, Maharastra (IN)

( * ) Notice: Subject to any disclaimer, the term of this patent is extended or adjusted under 35 U.S.C. 154(b) by 0 days.

(21) Appl. No.: 11/532,469

(22) Filed: Sep. 15, 2006

(65) Prior Publication Data
US 2007/0049749 A1    Mar. 1, 2007

Related U.S. Application Data

(63) Continuation of application No. 10/671,298, filed on Sep. 25, 2003, now abandoned.

(51) Int. Cl.
*C07D 501/04*   (2006.01)
*C07D 501/36*   (2006.01)

(52) U.S. Cl. .................................................. 544/227
(58) Field of Classification Search ............... 540/227
See application file for complete search history.

(56) References Cited

U.S. PATENT DOCUMENTS

| | | | | | |
|---|---|---|---|---|---|
| 4,423,213 | A | * | 12/1983 | Takaya et al. | 540/215 |
| 4,427,674 | A | * | 1/1984 | Takaya et al. | 514/202 |
| 4,452,851 | A | * | 6/1984 | Takaya et al. | 514/205 |
| 4,463,172 | A | * | 7/1984 | Horii et al. | 540/227 |
| 4,585,860 | A | * | 4/1986 | Takaya et al. | 514/202 |
| 5,026,843 | A | * | 6/1991 | Riccardo et al. | 540/227 |
| 5,109,131 | A | * | 4/1992 | Naito et al. | 540/227 |
| 6,384,215 | B1 | * | 5/2002 | Deshpande et al. | 540/227 |
| 6,458,949 | B1 | * | 10/2002 | Handa et al. | 540/226 |
| 6,552,186 | B2 | * | 4/2003 | Gerlach et al. | 540/222 |
| 6,919,449 | B2 | * | 7/2005 | Deshpande et al. | 540/222 |
| 2005/0027118 | A1 | * | 2/2005 | Deshpande et al. | 540/223 |
| 2005/0059821 | A1 | * | 3/2005 | Datta et al. | 540/227 |
| 2005/0065316 | A1 | * | 3/2005 | Sikes | 528/322 |
| 2005/0119478 | A1 | * | 6/2005 | Monguzzi et al. | 540/227 |
| 2008/0200670 | A1 | * | 8/2008 | Datta et al. | 540/227 |

FOREIGN PATENT DOCUMENTS

| | | | |
|---|---|---|---|
| EP | 30294 | A2 * | 6/1981 |
| EP | 556768 | A2 * | 8/1993 |
| EP | 842937 | A2 * | 5/1998 |
| WO | WO 0063214 | A1 * | 10/2000 |
| WO | WO 2004058695 | A1 * | 7/2004 |

* cited by examiner

*Primary Examiner*—Mark L Berch
(74) *Attorney, Agent, or Firm*—Kelley Drye & Warren LLP

(57) ABSTRACT

An improved process for preparation of ceftriaxone sodium of formula (II),

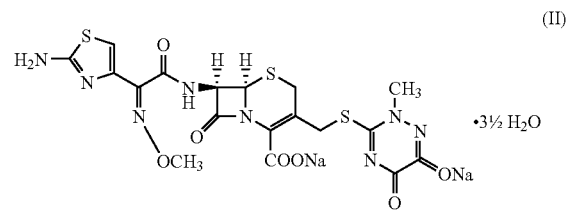

is disclosed.

21 Claims, No Drawings

METHOD FOR MANUFACTURE OF CEFTRIAXONE SODIUM

CROSS-REFERENCE TO RELATED APPLICATIONS

This is a continuation application of U.S. Ser. No. 10/671,298, filed Sep. 25, 2003, which claims priority from Indian Application Number 967/MUM/2003, filed Sep. 17, 2003. The disclosure of each such application is hereby incorporated by reference in its entirety where appropriate for teachings of additional or alternative details, features, and/or technical background, and priority is asserted from each.

FIELD OF THE INVENTION

The present invention relates to an improved method for manufacture of ceftriaxone sodium of high purity, high stability and low absorbance, rendering it highly amenable for formulation into a suitable dosage form.

BACKGROUND OF THE INVENTION

[6R-[6α,7β(Z)]]-7-[[(2-Amino-4-thiazolyl)(methoxyimino)acetyl]amino]-8-oxo-3-[[(1,2,5,6-tetrahydro-2-methyl-5,6-dioxo-1,2,4-triazin-3-yl)thio]methyl]-5-thia-1-azabicyclo[4.2.0]oct-2-ene-2-carboxylic acid or (6R,7R)-7-[2-(2-amino-4-thiazolyl)glyoxylamido]-3-[[(2,5-dihydro-6-hydroxy-2-methyl-5-oxo-as-triazin-3-yl)thio]methyl-8-oxo-5-thia-1-azabicyclo[4.2.0]oct-2-ene-2-carboxylic acid, generically known as ceftriaxone of formula (I) is a third generation cephalosporin antibiotic for parenteral administration.

(I)
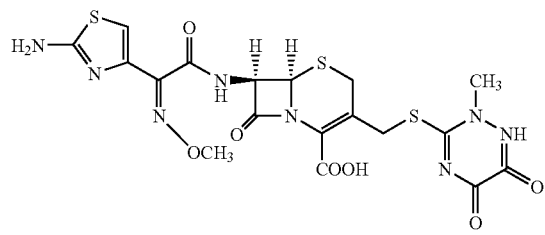

It is commercially sold as the disodium hemiheptahydrate salt of formula (II), commonly referred to as ceftriaxone sodium, under the brand names Rocefin® and Rocephin(e)®.

(II)
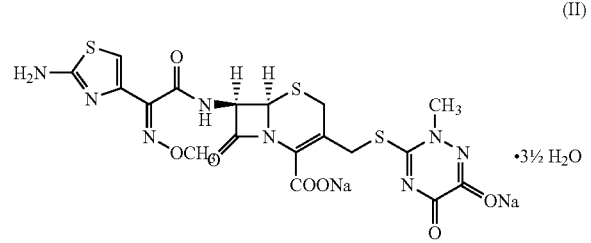

Ceftriaxone sodium is the largest-selling intravenous (iv) cephalosporin antibiotic worldwide and has been safely prescribed for over 15 years in both adults and children. This broad spectrum antibiotic exhibits remarkable activity against Gram-positive and Gram-negative bacteria, organisms responsible for the majority of community-based infections. These include upper and lower respiratory tract infections, including otitis media, sinusitis, bronchitis and community-acquired pneumonia as well as soft tissue infections. These infections result in nearly 80 million treated patients in the United States alone. Ceftriaxone is primarily used to treat hospital in-patients.

Because of its therapeutic and commercial importance, there is always a demand for a process for manufacture of ceftriaxone sodium on industrial scale, which gives the product not only in high yield but also of superior quality and stability, thereby rendering it highly amenable for formulation into a suitable dosage form.

Ceftriaxone of formula (I) has generally been synthesised by two methods as described in the art. Both the methods involve amidification of the 7-amino function of 7-amino-3-[2,5-dihydro-6-hydroxy-2-methyl-5-oxo-as-triazin-3-yl]-3-cephem-4-carboxylic acid derivative of formula (A) either directly with (Z)-2-(2-amino thiazol-4-yl)-2-methoxyimino acetic acid or its reactive derivatives thereof of formula (B) [Method-I] or with a (Z)-4-halo-2-methoxyimino-butyric acid derivative of formula (C) to give a 7-substituted cephalosporin addendum of formula (D), which on reaction with thiourea forms the (Z)-2-(2-amino thiazol-4-yl)-2-oxyimino acetamido side chain and thereby, provide ceftriaxone of formula (I), after necessary deprotections, if any of protective groups [Method-II]. The ceftriaxone (I) thus obtained is converted to the sodium salt of formula (II) by methods known in the art. The two methods of synthesis are summarized in Scheme-I.

In compounds of formula (A), (B), (C) and (D) of Method-I and II, the meanings of the groups R, $R_1$ and X are as defined therein and the groups Y and Z represent hydrogen or a group which forms a basis that compound of formula (B) and (C) are in a reactive form.

As per Method-I, synthesis of ceftriaxone (I) has been achieved by several ways, all differing in the choice of the reactive group Y. The following prior art methods illustrate the synthesis of ceftriaxone utilizing different reactive species as embodied in the group Y. These are, to name a few achieved through:

(i) Activation of the carboxylic acid (B, wherein Y=H) as the acid halide, as disclosed in Japanese Patent Nos. JP 52-102096, JP 53-157596 and British Patent No. GB 2,025,933. The acid halide, in particular the acid chloride is prepared by reaction of the 2-(2-amino thiazol-4-yl)-2-oxyimino acetic acid with $PCl_3$, $PCl_5$, $SOCl_2$ or $POCl_3$.

(ii) Activation of the carboxylic acid (B, wherein Y=H), through formation of its mixed anhydride, an active amide or an active ester, as disclosed in EP Patent No. 0,045,525.

(iii) Activation of the carboxylic acid (B, wherein Y=H), through formation of the activated ester by reaction of the carboxylic acid group with an acyloxyphosphonium chloride derivative, as disclosed in U.S. Pat. No. 5,317,099. The method of preparation comprises reacting the corresponding carboxylic acid derivative with triphenyl phosphine, hexachloroethane or carbon tetrachloride. However, this method increases the overall cost of the coupling reaction since it involves the use of expensive triphenyl phosphine.

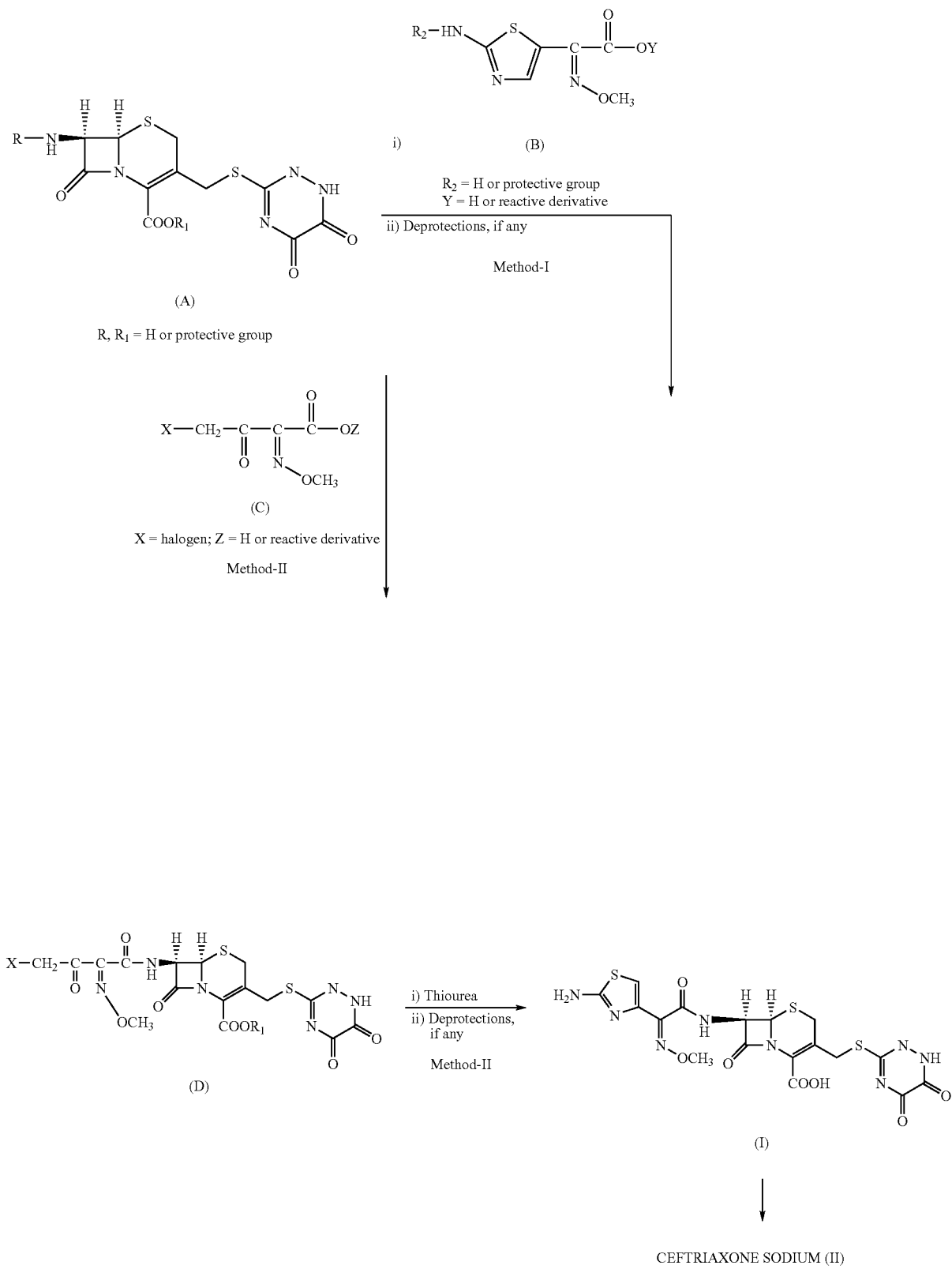
Scheme-I: Prior are methods for preparation of ceftriaxone (I)

(iv) Activation of the carboxylic acid (B, wherein Y=H), through formation of the activated benzothiazolyl thioester, in turn prepared by reaction of the carboxylic acid compound with bis[benzothiazolyl-(2)]disulfide and triphenyl phosphine, as disclosed in EP Patent Nos. EP 0 037 380. This method, however, utilizes expensive triphenyl phosphine for preparation of the activated ester.

(v) Activation of the carboxylic acid (B, wherein Y=H), by derivatisation with dimethyl formiminium chloride chlorosulfite (DFCS), as disclosed in U.S. Pat. No. 5,037,988. The dimethyl formiminium chloride chlorosulfite (DFCS) is in turn prepared by reacting equimolar quantities of thionyl chloride and N,N-dimethylformamide at room temperature. The method however, suffers from a drawback in that the amide forming reaction, utilizing the said activated reactive derivative can be effected in only specific solvents like benzene and toluene.

(vi) Activation of the carboxylic acid (B, wherein Y=H), by derivatisation with N,N dimethyl formiminium chloride chlorosulphate (DFCCS), as disclosed in U.S. Pat. No. 5,739,346. The N,N dimethyl formiminium chloride chlorosulphate (DFCCS) is in turn prepared by reacting equimolar quantities of sulfuryl chloride and N,N dimethylformamide at room temperature.

(vii) Activation of the carboxylic acid (B, wherein Y=H), as the thiophosphoryl ester, as disclosed in U.S. Pat. No. 5,567,813.

(viii) Activation of the carboxylic acid (B, wherein Y=H), as a 2-mercapto-5-substituted-1,3,4-oxadiazole derivative as disclosed in U.S. Pat. No. 6,388,070.

Synthesis of ceftriaxone (I) as per Method-II is equally widely documented in the literature. Several methods, varying subtly in the choice of the reactive group Z of compounds of formula (C) have been utilised, albeit the choice of the activating group is primarily restricted to acid halides. A few such methods are:

(a) U.S. Pat. No. 5,109,131 describes a process for preparation of 7-[2-(2-amino thiazol-4-yl)-oxyimino acetamido cephalosporin compounds, carrying a "residue of a nucleophile" in the 3α-position, which includes inter alia ceftriaxone. The method utilizes tert-butyl-3-oxobutyrate as an intermediate, which is reacted as such or a reactive derivative thereof is reacted with compound of formula (A) to form the 7-substituted cephalosporin addendum (D), which on reaction with thiourea gives ceftriaxone. The reactive derivatives utilised for 7-amidification as disclosed in U.S. Pat. No. 5,109,131 include acid halides, a mixed acid anhydride, an active amide or an active ester. The chemistry is summarized as shown hereinbelow in Scheme-I1

(b) European Patent No. 0,030,294 (and its equivalent in Canada, CA 1 146 165) claims ceftriaxone and its esters and a process for preparation thereof comprising the following steps as described in Example-1 of said patent i.e.

b.1 reacting (7R)-Amino-3-desacetoxy-3-[(2,5-dihydro-6-hydroxy-2-methyl-5-oxo-as-triazin-3-yl)thio] methyl-3-cephem-4-carboxylic acid (corresponding to Compound A of Scheme-I) with N,O-bis-(trimethylsilyl)-acetamide in ethyl acetate at 25° C. for 30 minutes to form the corresponding (N,O)-bis-silyl derivative;

b.2 addition of a solution of 4-bromo-2-methoxyimino-3-oxo-butyryl chloride (Corresponding to Compound C of Scheme-I) in dichloromethane to the solution of the (N,O)-bis-silyl derivative in ethyl acetate thus obtained in step b.1 and after work up, crystallization of the residue from etherpetroleum ether to give (6R, 7R)-7-[[4-Bromo-2-(Z)-methoxyimino]acetamido]-3-[(2,5-dihydro-6-hydroxy-2-methyl-5-oxo-as-triazin-3-yl)thio]methyl-3-cephem-4-carboxylic acid [corresponding to compound (D) of Scheme-I];

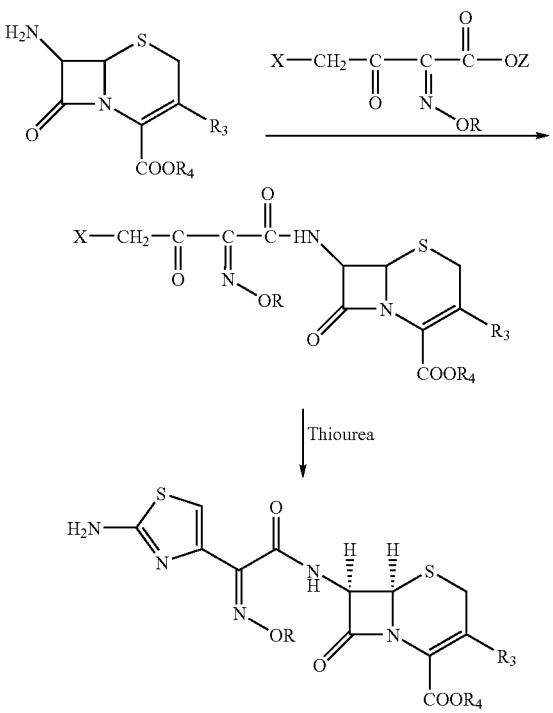

Scheme-II: Process disclosed in U.S. Pat. No. 5 109 131

R = alkyl;
$R_3$ = H or standard cephalosporin substituent, specially a residue of nucleophile;
$R_4$ = H or a group which can be converted to hydrogen under mild acidic or alkaline condition or eliminated by means of oxidation or reduction b.3 reaction of the (6R,7R)-7-[[4-Bromo-2-(Z)-methoxyimino]acetamido]-3-[(2,5-dihydro-6-hydroxy-2-methyl-5-oxo-as-triazin-3-yl)thio]methyl-3-cephem-4-carboxylic acid obtained above with thiourea in absolute alcohol to give the hydrobromide salt of ceftriaxone; and b.4 neutralisation of ceftriaxone hydrobromide salt with sodium methoxide in a mixture of water and acetone to give ceftriaxone (I), which is isolated by filtration.

The chemistry disclosed in EP Patent No. 0,030,294 is summarized in Scheme-III.

(c) European Patent No. 0,842,937 claims a process for preparation of ceftriaxone and cefotaxime comprising reaction of 7-amino-3-desacetoxy-3-[2,5-dihydro-6-hydroxy-2-methyl-5-oxo-as-triazin-3-yl)-thio]-3-cephem-4-carboxylic acid (compound III of Scheme-I) and 7-ACA respectively with 4-chloro-2-methoxyimino-3-oxobutyric acid, activated as 2-mercaptobenzothiazolyl ester, followed by cyclization of the intermediate thus obtained with thiourea to give ceftriaxone and cefotaxime respectively. The chemistry disclosed in EP Patent No. 0,842,937 is summarized in Scheme-IV.

Scheme-III: Method of preparation of ceftriaxone as disclosed in EP Patent No. 0 030 294
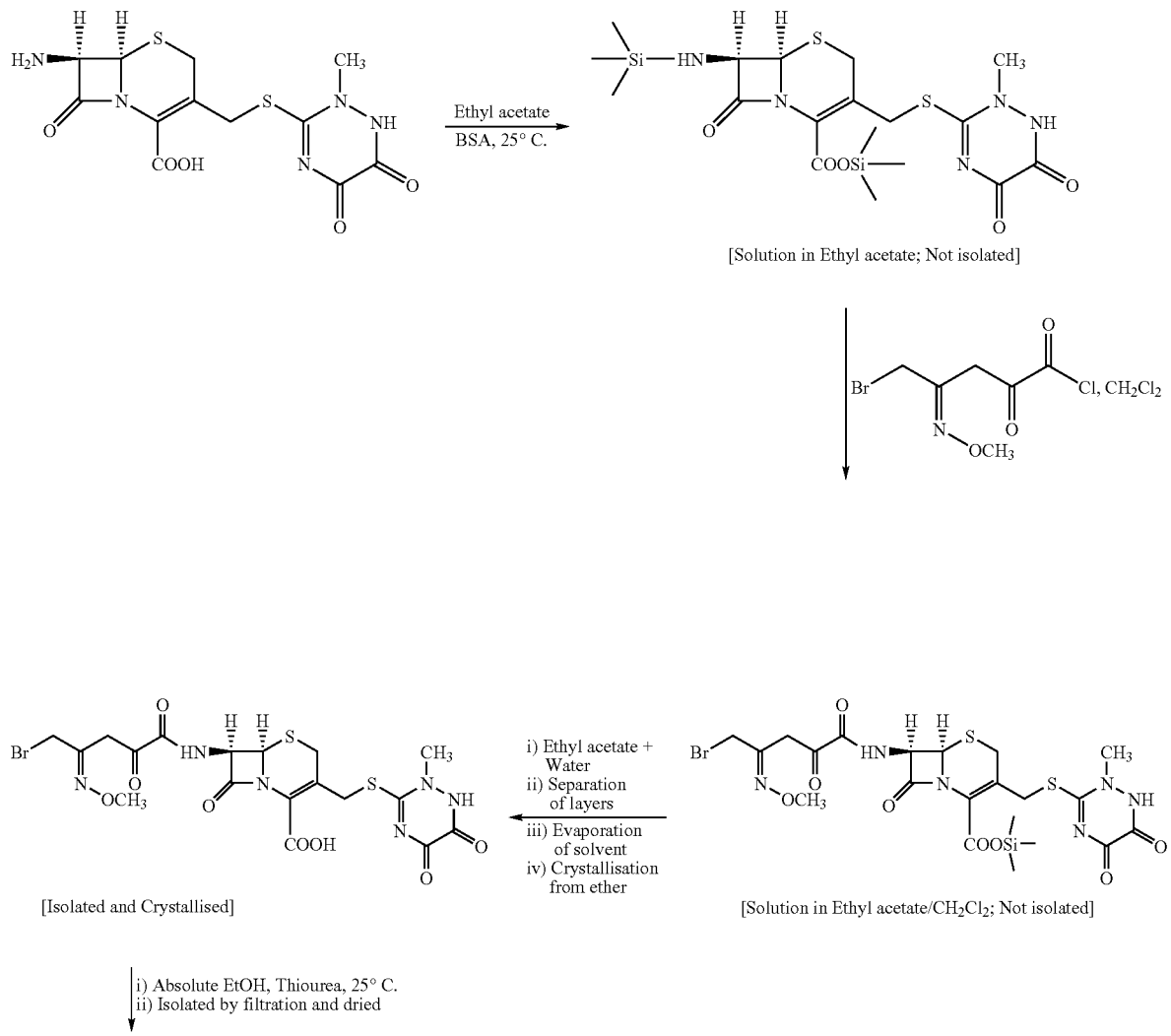
[CEFTRIAXONE HYDROBROMIDE SALT]
i) Acetone + Water, NaOCOCH₃
ii) Isolation by filtration
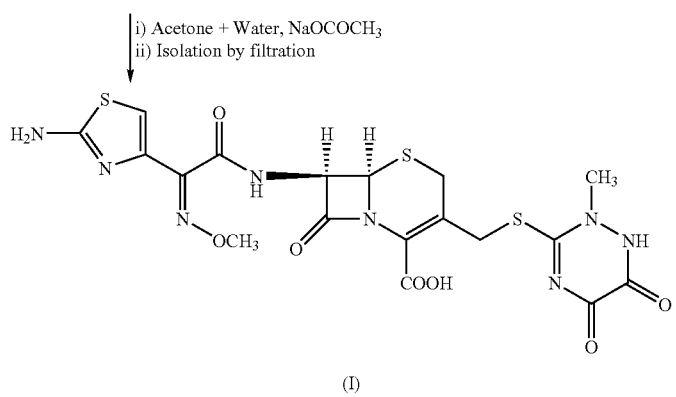
(I)

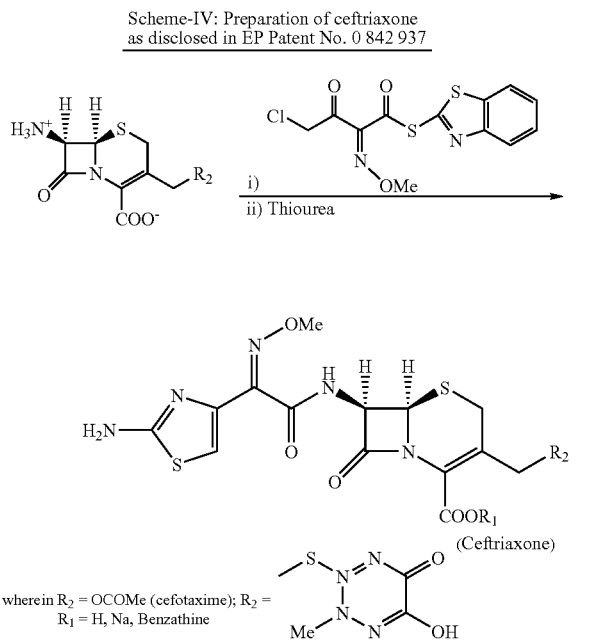

Scheme-IV: Preparation of ceftriaxone as disclosed in EP Patent No. 0 842 937 wherein $R_2$ = OCOMe (cefotaxime); $R_2$ = [triazinylthio group]; $R_1$ = H, Na, Benzathine (d) The process disclosed in EP Patent No. 0,556,768 essentially is an improvement over the one described in EP Patent No. 0,842,937, wherein the method for preparation of ceftriaxone comprises reaction of 7-amino-3-desacetoxy-3-[2,5-dihydro-6-hydroxy-2-methyl-5-oxo-as-triazin-3-yl)-thio]-3-cephem-4-carboxylic acid (compound A of Scheme-I) with 4-chloro-2-methoxyimino-3-oxobutyric acid, activated as 2-mercaptobenzothiazolyl ester, followed by cyclization of the intermediate thus obtained with thiourea to give ceftriaxone. The improvement this patent claims is that the above-mentioned reaction and subsequent conversion of ceftriaxone to its disodium hemiheptahydrate salt can be carried out in one pot using a mixture of acetone and water as solvent.

(e) U.S. Pat. No. 6,384,215 provides yet another variation, wherein the compound V of Scheme-I is activated as a 2-mercapto-5-substituted-1,3,4-oxadiazole derivative prior to 7-amidification, followed by cyclization of the intermediate compound thus obtained with thiourea to give ceftriaxone, (f) The recently issued U.S. Pat. No. 6,552,186 B2 claims a method for preparation of ceftriaxone comprising reaction of (N,O)-bis silylated 7-amino-3-desacetoxy-3-[2,5-dihydro-6-hydroxy-2-methyl-5-oxo-as-triazin-3-yl)-thio]-3-cephem-4-carboxylic acid (compound A of Scheme-I) with 4-halo-2-methoxyimino-3-oxobutyric acid, suitably activated as a reactive derivative (compound C of Scheme-I) to give the corresponding intermediate 7-acylated compound (D of Scheme-I, wherein the group $R_1$ attached to the carboxylic acid function at the 4-position is a trialkyl silyl group), followed by either, (i) reaction of the 7-acylated compound (D of Scheme-I, wherein the group $R_1$ attached to the carboxylic acid function at the 4-position is a trialkyl silyl group), with silylated thiourea to form the aminothiazole ring, which after necessary desilylation gives ceftriaxone, (as claimed in claim 3a of said patent); or (ii) desilylation of the 7-acylated compound (D of Scheme-I, wherein the group $R_1$ attached to the carboxylic acid function at the 4-position is a trialkyl silyl group), followed by reaction of the desilylated compound thus obtained with thiourea to give ceftriaxone (as claimed in claim 3a of said patent).

In addition, the U.S. Pat. No. 6,552,186 B2, claims the 7-acylated compound (D of Scheme-I, wherein the group $R_1$ attached to the carboxylic acid function at the 4-position is a trialkyl silyl group) as represented in Chart-I hereinbelow as a novel compound.

Chart-I: Compound claimed in claim 1 of U.S. Pat. No. 6,552,186 B2

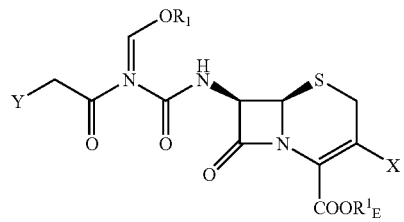

wherein
$R_1$ is unsubstituted alkyl or alkyl
$R^1_E$ is trialkyl silyl or denotes with the COO⁻ to which $R^1_E$ is attached is an ester
Y = halogen
X is a group of formula
R″ is trialkyl silyl

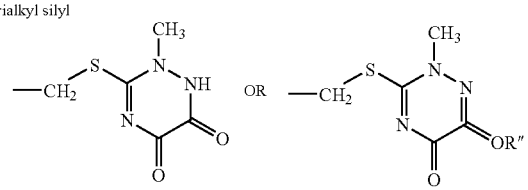

The U.S. Pat. No. 6,552,186 B2 further claims that the reaction of the desilylated compound with thiourea is effected in the presence of a solvent system containing an organic solvent and water to give ceftriaxone. The chemistry claimed in claims 3a and 3a¹ of the U.S. Pat. No. 6,552,186B2 for synthesis of ceftriaxone is summarized in Scheme-V. However, the chemistry embodied in claim 3a¹ of the U.S. Pat. No. 6,552,186 B2 not only lacks novelty but is anticipated from the prior art methods discussed hereinbefore as well as those summarized hereinbelow, as would be apparent to a person skilled in the art from the discussion contained hereinbelow:

f.1 The invention apparently residing in U.S. Pat. No. 6,552,186 B2 is use of a silylated compound i.e. (6R,7R)-7-[[4-Bromo-2-(Z)-methoxyimino]acetamido]-3-[(2,5-dihydro-6-hydroxy-2-methyl-5-oxo-as-triazin-3-yl)thio]methyl-3-cephem-4-carboxylic acid, wherein the carboxylic acid function is silylated for subsequent reaction with, (a) silylated thiourea to give ceftriaxone after desilylation (as claimed in Claim 3a of said patent); or (b) desilylation of the silyl compound and reaction of the desilylated compound thus obtained with thiourea to give ceftriaxone (as claimed in Claim 3a¹ of said patent).

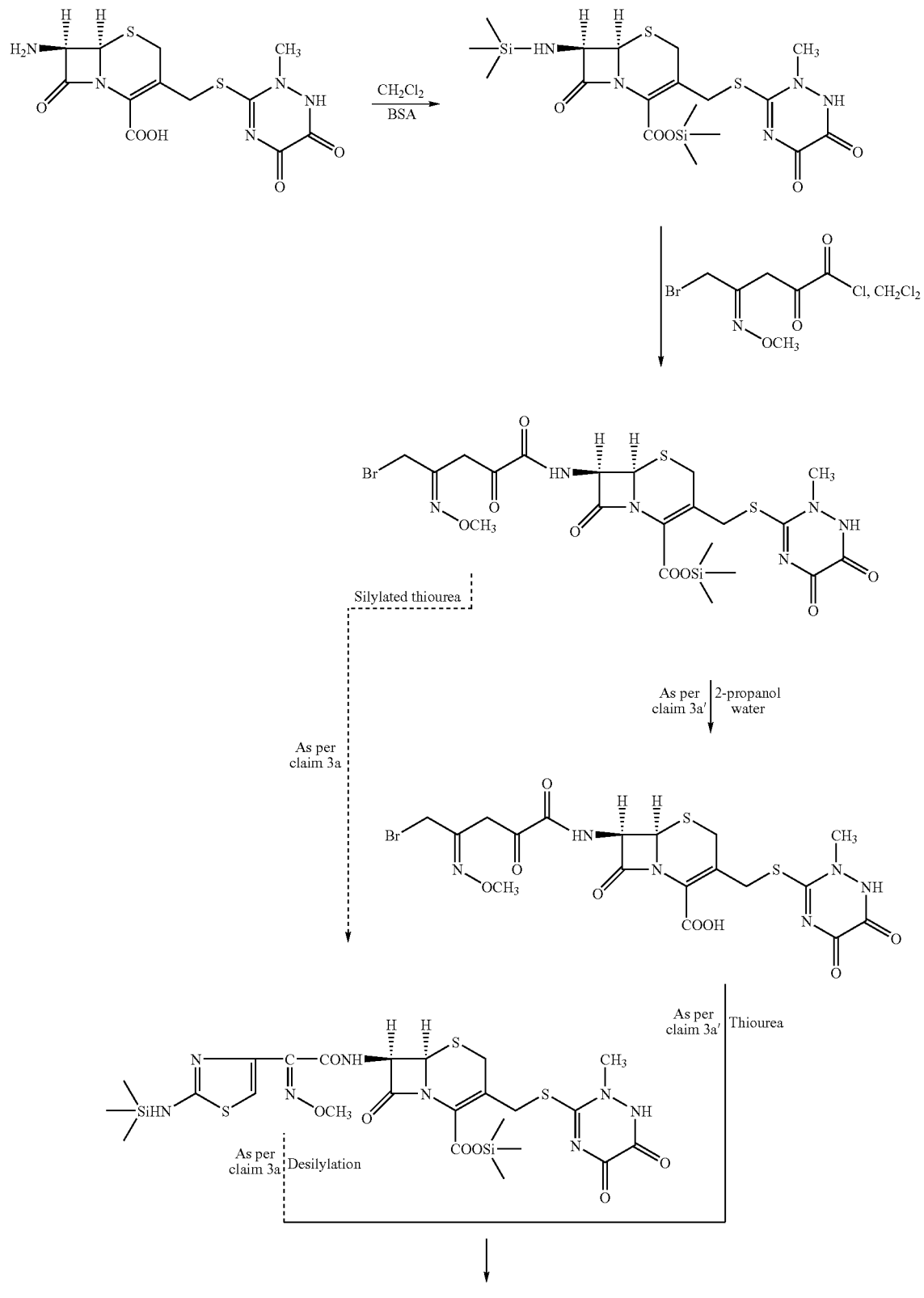

f.2 However, the said chemistry is identical and superimposable to that disclosed in Example-1 of EP Patent No. 0,030,294, summarized in Scheme-III, which, needless to mention has an early priority of nearly twenty years than the priority date of U.S. Pat. No. 6,552,186 B2.

The only difference in both the processes is in the choice of solvents, reaction temperatures and mode of isolation of the product. However, both the methods function the same way giving substantially the same result, thereby indicating that the change in parameters and solvents are inconsequential and have no bearing in the course of the reaction, f.3 Moreover, the compound claimed in claim 1 of U.S. Pat. No. 6,552,186 B2 (as summarized in Chart-I) lacks novelty since the same compound is obtained and reported, albeit not specified in the process embodied in Example-1 of EP Patent No. 0,030,294.

f.4 Further, that portion of claim 3a[1] of U.S. Pat. No. 6,552,186 B2 claiming that the reaction of the desilylated compound with thiourea is effected in the presence of a solvent system containing an organic solvent and water to give ceftriaxone also is anticipated from the teachings of U.S. Pat. No. 5,109,131, wherein a mixture of organic solvent and water i.e. mixture of tetrahydrofuran and water has been specified and used for cyclization of a structurally similar compound with thiourea for formation of the aminothiazolyl addendum at the 7-amino position, as evident from WORKING EXAMPLE; 3 (4), column 13 of said patent, f.5 With regard to protection of the carboxylic acid function at 4-position of a cephalosporonic acid derivative as a trialkylsilyl group prior to amidification at 7-position as claimed in Claim 3a[1] of U.S. Pat. No. 6,552,186 B2 it can be termed at the most "trivial" and not substantially contributing to the development of cephalosporin chemistry in any way. Similarly, deprotection of the said "trialkylsilyl" protective group is also "trivial" and has no substantial bearing in the course of the reaction.

There is a wealth of literature, wherein the carboxylic acid function at 4-position and/or the amino function at 7-position of a cephalosporin derivative have been protected through silylated derivatives prior to amidification. From these, it would be abundantly evident that claims for protection and deprotection through silylation residing in U.S. Pat. No. 6,552,186 B2 is not novel and is anticipated and obvious to a person skilled in the art. Protection of reactive functional groups, specially the carboxylic acid function at 4-position and the amino function at 7-position through silylation is widely practiced in cephalosporin chemistry since many years. As early as 1964 acylation of 6-aminopenicillinate esters (6-APA) to give commercially valuable antibiotics such as ampicillin and amoxycillin have been achieved through protection of the carboxylic acid function at 3-position as trialkyl silyl esters [Glombitza, K. W., *Ann*, 1964, 166].

This publication teaches acylation of 6-aminopenicillinate (6-APA) esters having an easily removable carboxyl protecting group and, therefore, soluble in organic solvents. The author discovered that 6-APA trialkyl silyl esters could be readily obtained by reacting 6-APA with hexamethyldisilazane in chloroform and the ester thus obtained could be successfully acylated with acid chlorides or by the mixed anhydride method. The advantage cited is that the silyl group could be removed merely by treatment with water during the workup procedure. Several penicillins were synthesized in high yields (65-98%) by this method, which is summarized in Scheme-VI.

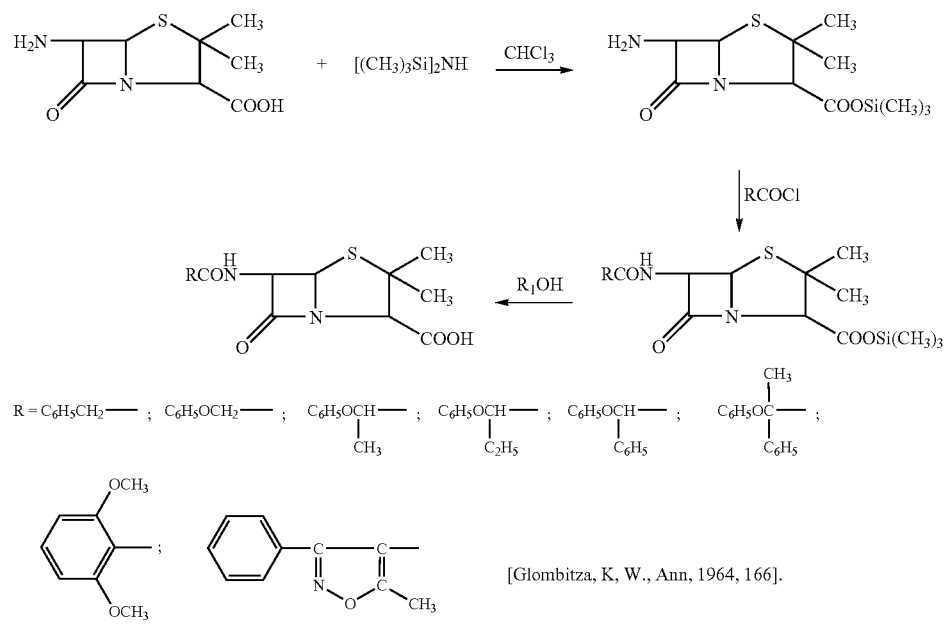

Scheme-VI: The acylation of penicillins as disclosed by Glombitza, K. W. in Ann, 1964, 166

[Glombitza, K, W., Ann, 1964, 166].

Similarly, an improved method for preparation of 7-acylamidocephalosporanic acids by acylation of the 7-ACA esters was reported as early as 1963, wherein the inventors have claimed that best results were achieved by silyl esters of 7-ACA since the ester group was easily removed by mild acidic work-up (Jackson et. al., GB Patent No. 1,073, 530).

This patent teaches an improved procedure for the preparation of 7-acylamidocephalosporanic acids by acylating the 7-ACA esters which are soluble in organic solvents. The patent claims that best results were achieved by using the silyl esters of 7-ACA since the ester group was easily removed by mildly acidic conditions during the workup procedure.

The chemistry is summarized in Scheme-VII.

Scheme-VII: the acylation of cephalosprins disclosed in GB Patent N. 1 073 530

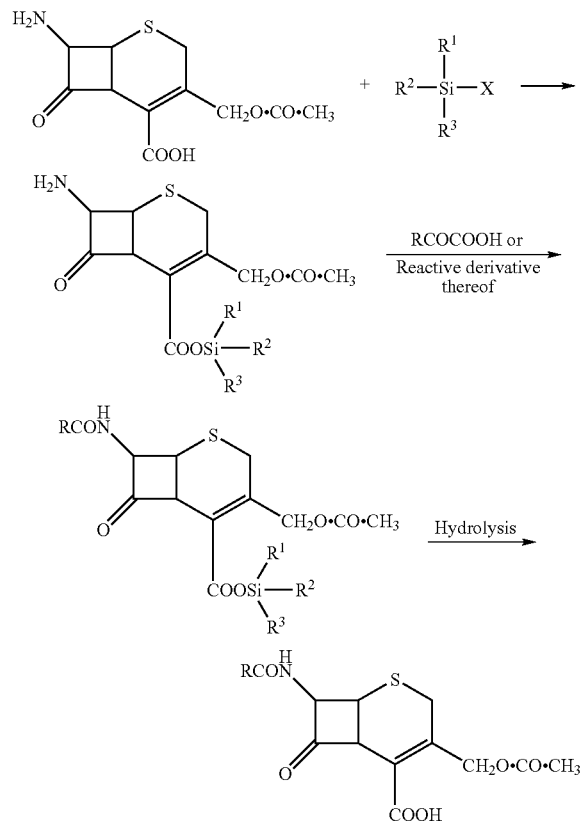

$R^1$, $R^2$, $R^3$ = Alkyl group of 1-6 carbon atom; X = halogen or a group $NR^4R^5$, wherein $R^4$ and $R^5$ are hydrogen or an alkyl group 1-6 carbon or a group

(g) In addition, replication of the prior art methods, specially the process embodied in Example-2 of U.S. Pat. No. 6,552,186 B2 for preparation of ceftriaxone sodium is found to be associated with the following shortcomings in that:

g.1 the reaction (N,O)-bis trialkylsilyl 7-amino-3-[2,5-dihydro-6-hydroxy-2-methyl-5-oxo-as-triazin-3-yl]-3-cephem-4-carboxylic acid with 4-halo-2-methoxy-imino-3-oxo-butyric acid halide to give (6R,7R)-7-[[4-halo-2-(Z)-methoxyimino]acetamido]-3-[(2,5-dihydro-6-hydroxy-2-methyl-5-oxo-as-triazin-3-yl)thio]methyl-3-cephem-4-carboxylic acid trialkylsilyl ester, does not proceed to completion and about 10% of starting compound i.e (N,O)-bis trialkylsilyl 7-amino-3-[2,5-dihydro-6-hydroxy-2-methyl-5-oxo-as-triazin-3-yl]-3-cephem-4-carboxylic acid remains unreacted, g.2 precipitation of ceftriaxone occuring during reaction of (6R,7R)-7-[[4-halo-2-(Z)-methoxyimino]acetamido]-3-[(2,5-dihydro-6-hydroxy-2-methyl-5-oxo-as-triazin-3-yl)thio]methyl-3-cephem-4-carboxylic acid (after subsequent hydrolysis of the trialkylsilyl carboxylic ester) with thiourea, which not only because of the incompletion of reaction in the precursor step but also because of formation of higher level of impurities in the reaction result in production of ceftriaxone in lower yield, and of unsatisfactory quality and g.3 conversion of ceftriaxone thus produced to ceftriaxone sodium is found to give a colored product i.e. very high color absorbance of 1.0 to 1.8 AU at 450 nm, having a purity of about 73-80%, and containing higher level of impurities, all contributing to and resulting in production of ceftriaxone and ceftriaxone sodium of quality and nature not conforming to pharmacopoeial specifications and therefore, rendering the product not only unsuitable for formulation into a dosage form but also for administration to human beings.

Further, replication of the methods described in other prior art methods, mentioned hereinbefore also were found to afford the product in unsatisfactory yields and quality, rendering them less cost-effective.

Thus, from the foregoing it would be apparent that there is a need for a method for manufacture of ceftriaxone (I) and ceftriaxone sodium (II), not only in a cost-effective manner but with vastly improved stability, high purity, and excellent physical characteristics, such as flowability and color absorbance.

It is therefore, an object of the present invention to provide a cost-effective method for manufacture of ceftriaxone sodium in high yield, possessing high purity, improved stability, low color absorbance, hitherto not been achieved in prior art.

The present inventors have found that such an objective could be achieved through a selection of the right quality of reactants, type of solvents, pH, other reaction conditions or parameters etc., which are surprising findings, thus forming the inventive step of the present invention.

In particular, the present inventors have found that the level of impurities in the finished product i.e. ceftriaxone sodium, in turn arising out of their formation at various stages of the process could be minimized, the efficiency of the reaction at each stage of the chemical sequence could be enhanced and the color absorbance of the finished product could be drastically improved and ceftriaxone of formula (I) could be obtained in high purity in one pot and converted to ceftriaxone sodium of formula (II), possessing the desired object characteristics, through a selection of the night quality of reactants, type of solvents, pH, other reaction conditions or parameters etc., when:

(a) a 4-halo-2-methoxyimino-3-oxo-butyric acid halide derivative having a purity of at least 95%, preferably of about 97-98%, containing less than 0.50% of di-and polybrominated compounds and preferably prepared and purified as per the method disclosed in our published PCT Application No. WO 03/045899 A1, is utilized for reaction with (N,O)-bis trialkylsilyl 7-amino-3-[2,5-dihydro-6-hydroxy-2-methyl-5-oxo-as-triazin-3-yl]-3-cephem-4-carboxylic acid in the presence of a inert water-immiscible organic solvent to give (6R,7R)-7-[[4-halo-2-(Z)-methoxyimino]acetamido]-3-[(2,5-dihydro-6-hydroxy-2-methyl-5-oxo-as-triazin-3-yl)thio]methyl-3-cephem-4-carboxylic acid trialkylsilyl ester;

(b) the aforementioned reaction of 4-halo-2-methoxyimino-3-oxo-butyric acid halide derivative having the said purity with (N,O)-bis trialkylsilyl 7-amino-3-[2,5-dihydro-6-hydroxy-2-methyl-5-oxo-as-triazin-3-yl]-3-cephem-4-carboxylic acid in the presence of a inert water-immiscible organic solvent to give (6R,7R)-7-[[4-halo-2-(Z)-methoxyimino]acetamido]-3-[(2,5-dihydro-6-hydroxy-2-methyl-5-oxo-as-triazin-3-yl)thio]methyl-3-cephem-4-carboxylic acid trialkylsilyl ester is carried out in the presence an acid scavenging agent;

(c) in the hydrolysis of the trialkyl ester group of (6R,7R)-7-[[4-halo-2-(Z)-methoxyimino]acetamido]-3-[(2,5-dihydro-6-hydroxy-2-methyl-5-oxo-as-triazin-3-yl)thio]methyl-3-cephem-4-carboxylic acid trialkylsilyl ester to give the corresponding (6R,7R)-7-[[4-halo-2-(Z)-methoxyimino]acetamido]-3-[(2,5-dihydro-6-hydroxy-2-methyl-5-oxo-as-triazin-3-yl)thio]methyl-3-cephem-4-carboxylic acid, the said hydrolysis of the trialkylsilyl ester is effected, without its isolation from the reaction mixture with approximately a 1:1 mixture of water and a water-miscible organic solvent selected from tetrahydrofuran and acetonitrile, wherein the hydrolysed compound is portioned in the inert water-immiscible organic solvent phase;

(d) in the step of reaction of the solution of (6R,7R)-7-[[4-halo-2-(Z)-methoxyimino]acetamido]-3-[(2,5-dihydro-6-hydroxy-2-methyl-5-oxo-as-triazin-3-yl)thio]methyl-3-cephem-4-carboxylic acid in the inert water-immiscible organic solvent with thiourea, the said reaction is carried out in presence of water, the precipitation of ceftriaxone along with impurities is avoided by carrying out the reaction in the presence of an inorganic base selected from alkali metal containing inorganic bases, rather than an organic base and at a pH of between 5.0 to 5.5, which leads to formation of the alkali metal salt of ceftriaxone, wherein the said alkali metal salt of ceftriaxone thus formed is completely partitioned in the aqueous phase, and wherein it remains as a solution and does not separate out, while the associated impurities are selectively partitioned in the inert water-immiscible organic solvent phase. Neutralization of the alkali metal salt gives ceftriaxone in higher yield and substantially free of impurities, which is isolated; and (e) in the step of formation of ceftriaxone sodium, the ceftriaxone thus obtained is first converted to an amine salt by reaction with an organic amine, maintaining strictly a pH of 5.4±0.2 and reacting the amine salt thus formed without isolation with a sodium metal carrier to give ceftriaxone sodium in high yield, possessing high purity, containing impurities in the range of 0.05 to 0.20% and possessing low color absorbance in the range of 0.04-0.05 AU.

The effect of using a 4-halo-2-methoxyimino-3-oxo-butyric acid halide derivative having a purity of at least 95%, preferably having a purity of 97-98% and utilization of an acid scavenging agent in tandem in the reaction ensures not only completion of reaction but also in effective neutralization of hydrogen halide formed during the reaction, thereby contributing to the desired objective.

Similarly, the utilization of the right pH, the choice of the alkali metal inorganic base, the selection of the right water-miscible organic solvent in the subsequent steps also contributes in achieving the desired objective, overall providing a vastly improved method cost-effective method for manufacture of ceftriaxone of formula (I) and ceftriaxone sodium of formula (II).

SUMMARY OF THE INVENTION

In one aspect of the present invention, there is provided an improved one-pot process for preparation of ceftriaxone of formula (I), in high yield and purity,

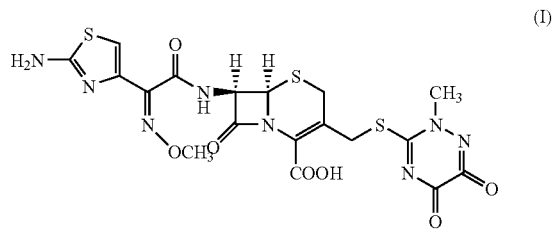

comprising the steps of (a) reacting a silylated compound of formula (III),

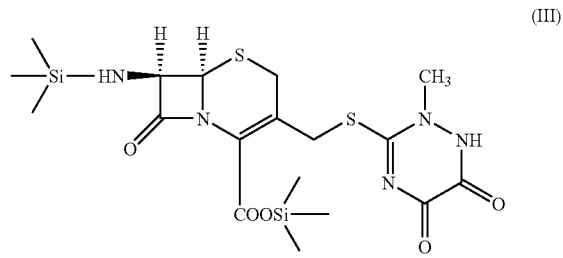

with a 4-halo-2-methoxyimino-3-oxo-butyric acid halide derivative of formula (IV), having a purity of at least 95%, preferably of about 97-98%, containing di- and poly-bromo compounds less than 0.50% and preferably prepared and purified as per the method disclosed in our published PCT Application No. WO 03/045899 A1,

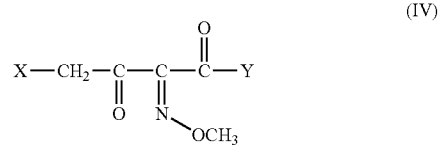

wherein X and Y represent a halogen atom in the presence of an inert water-immiscible organic solvent or mixtures thereof and in the presence of an acid scavenging agent at a temperature of between −10° C. to −60° C. to give a compound of formula (V),

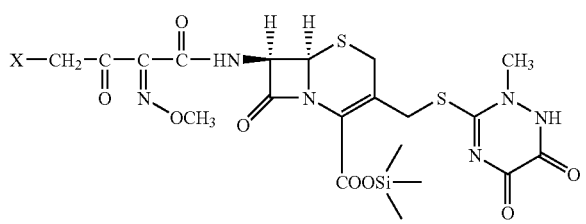

(b) adding the solution of compound of formula (V) in the inert water-immiscible organic solvent or mixtures thereof to a 1:1 mixture of water and a water-miscible organic solvent and separation of the organic phase to provide a solution of compound of formula (VI) in the inert water-immiscible organic solvent or mixtures thereof,

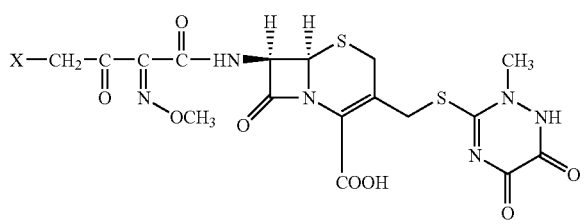

(c) reacting the solution of compound of formula (VI) in the inert water-immiscible organic solvent or mixtures thereof with a solution of thiourea in water in the presence of an alkali metal containing inorganic base at a temperature of between 0° C. to +10° C. at a pH ranging between 5.0 to 5.5 and separation of the layers to provide a solution of the alkali metal salt of ceftriaxone of formula (II$^1$) in water, wherein M is an alkali metal, substantially free of impurities, and

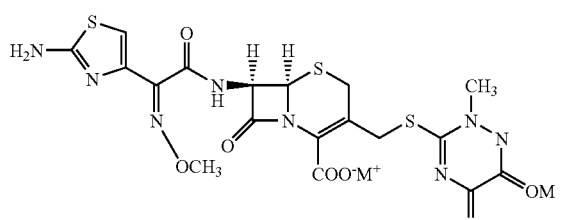

(d) mixing the solution of the alkali metal salt of ceftriaxone (II$^1$) in water with a water-immiscible organic solvent and a water-miscible solvent and treating the solution thus obtained with an acid to a pH of 3.6 to 4.0 and isolating the precipitated ceftriaxone of formula (I) in high purity, substantially free of impurities by filtration.

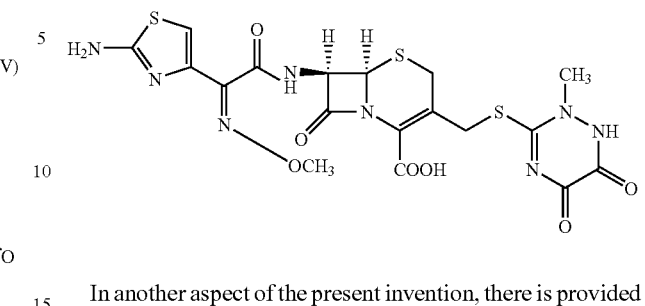

In another aspect of the present invention, there is provided a method of preparing ceftriaxone sodium of formula (II), in high purity, containing 0.05 to 0.20% of impurities and having a color absorbance of 0.04 to 0.05 AU at 450 nm

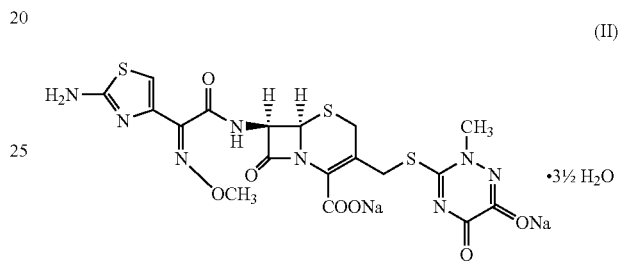

comprising
(a) reaction of a solution in water of ceftriaxone of formula (I) as obtained by the process of the present invention,

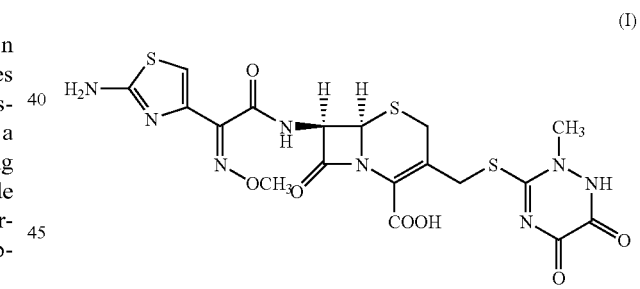

with an organic amine, maintaining a pH of 5.4±0.2 to produce a solution of the amine salt of ceftriaxone of formula (VII) in water,

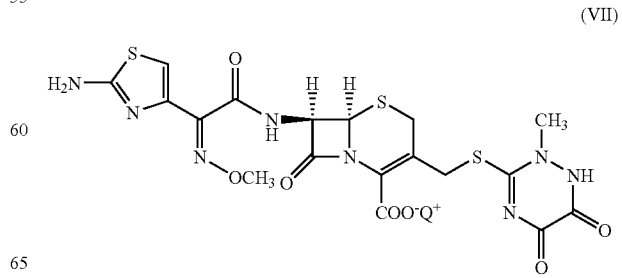

wherein Q represents the organic amine, and (b) reaction of the amine salt of ceftriaxone of formula (VII) in a mixture of water and a water-immiscible and a water-miscible organic solvent with a sodium metal carrier to give ceftriaxone sodium of formula (II) in high purity, containing 0.05 to 0.20% of impurities and having a color absorbance of 0.04 to 0.05 AU at 450 nm

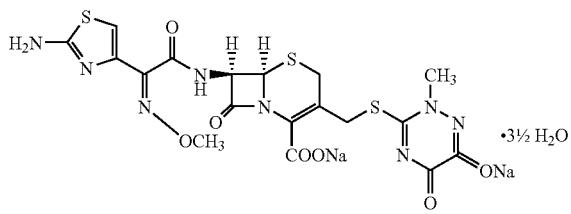

The process of this invention is summarized in Scheme-VIII for ready reference.

DETAILED DESCRIPTION OF THE INVENTION

The effect of the various selection of the right quality of reactants, type of solvents, pH, other reaction conditions or parameters etc., which forms the basis of the present invention in providing a one pot method for manufacture of ceftriaxone (I) and its conversion to ceftriaxone sodium (II) in high yield, possessing high purity, high stability, low color value, thereby rendering it highly amenable for formulation into a suitable dosage form and for administration to human beings is discussed in detail hereinbelow.

1. Effect of Quality of 4-halo-2-methoxyimino-3-oxo-butyric acid halide (IV)

Scheme-VIII: Preparation of ceftriaxone (I) and ceftriaxone sodium (II) as per the present invention

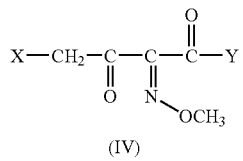

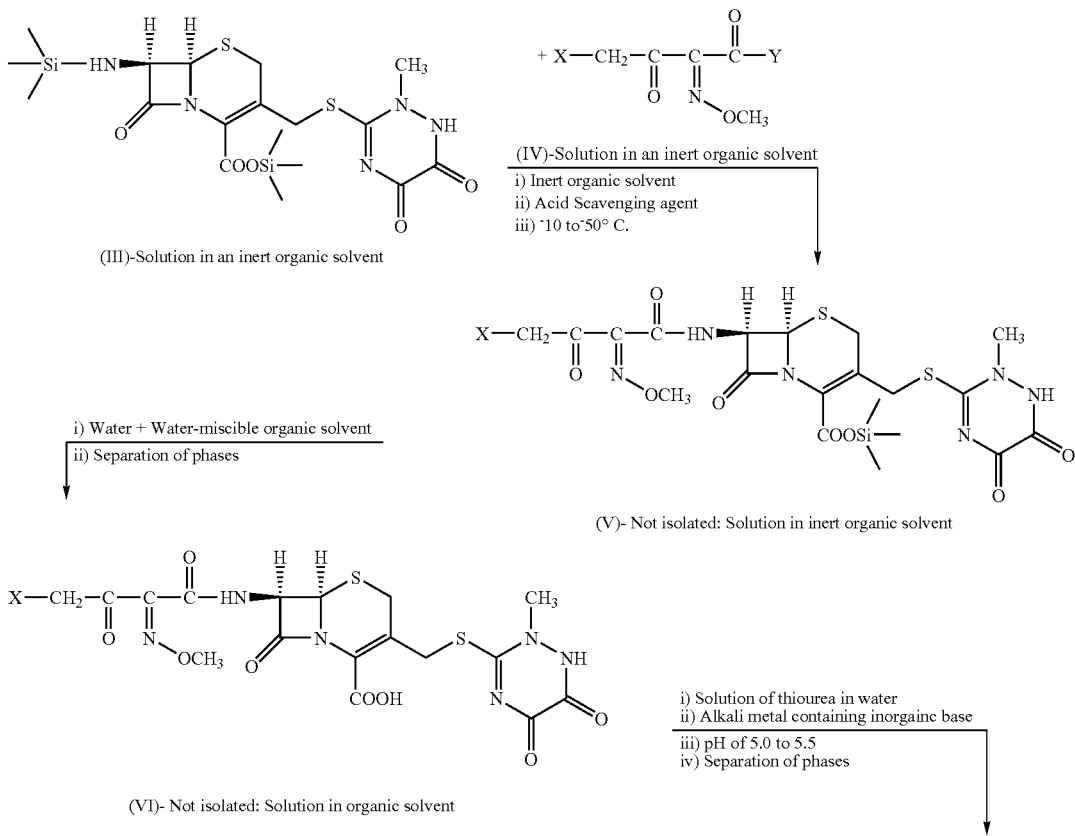

-continued
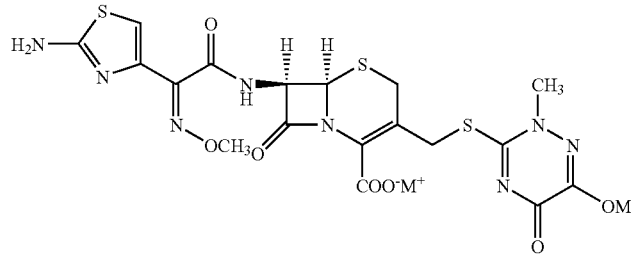
(II¹)- Not isolated: Aqueous solution
i) Water-miscible + Water-immiscible organic solvent
ii) H⁺; pH 3.6 to 4.0
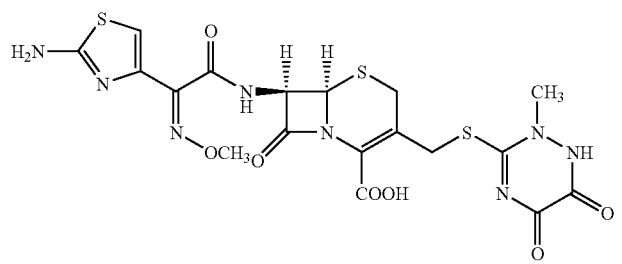
(I)- Isolated
i) Water, Amine
ii) pH of 5.5 ± 2.0
i) Water + Water-miscible organic solvent
ii) Sodium metal carrier
(VII)- Not Isolated: Aqueous solution
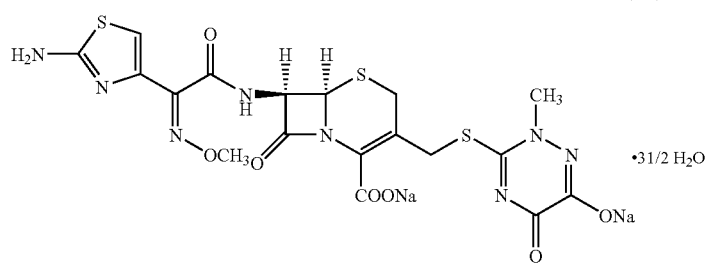
(II)- Isolated 4-halo-2-oxyimino-3-oxo-butyric acids, corresponding to compound of formula (IV), wherein X is halogen and Y is hydrogen, which are precursors for the acid halide compounds of formula (IV), wherein X and Y are halogen are known compounds and widely used for synthesis of cephalosporin antibiotics, carrying a 2-[(2-amino thiazol-4-yl)-2-oxyimino]acetamido side-chain at 7-position.

These compounds, wherein the halogen atom represented by the group X is chlorine, bromine or iodine are generally prepared by halogenation at 4-position of the corresponding 2-oxyimino-3-oxo-butyric acid or its esters of formula (IV$^1$) or by direct halogenation of diketene of formula (IV$^2$), the halogenated compound thus obtained further elaborated to compound of formula (IV).

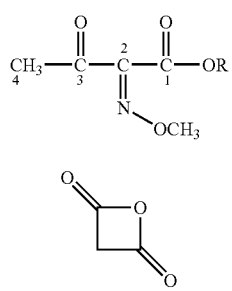

A detailed discussion of the subsisting prior art methods for preparation of 4-halo-2-oxyimino-3-oxo-butyric acids, corresponding to compound of formula (IV), wherein X is halogen and Y is hydrogen are summarized in our pending PCT Application published as WO 03/045899.

However, such prior methods are associated with several shortcomings, the major one being they invariably result in formation of considerable amounts of di- and poly-brominated derivatives (in the range of 2-3%) and other impurities, thereby giving the product i.e. 4-halo-2-oxyimino-3-oxo-butyric acids not only in low yields but also of inferior quality. Subsequent purification results in considerable loss of the desired product, rendering such methods commercially unattractive. Moreover, such halo acids, are not suitable for synthesis of cephalosporin antibiotics, carrying a 2-[(2-amino thiazol-4-yl)-2-oxyimino]acetamido side-chain at 7-position and result in production of such antibiotics in lower yields (WO 03/045899).

An improved method for preparation of 4-halo-2-oxyimino-3-oxo-butyric acids, corresponding to compound of formula (IV), wherein X is halogen and Y is hydrogen was disclosed in WO 03/045899, wherein the said halo acid compound is obtained substantially free of di- and poly-brominated compounds, typically less than 0.5% and other impurities.

The product after a simple crystallization was obtained in a purity of at least 95%, typically in a purity of 97-98%.

In the present context, it is found highly advantageous to utilize the halo acid as prepared by the method described in WO 03/045899 for synthesis of ceftriaxone sodium (II), which not only leads to completion of reaction, but also is substantially free of impurities resulting in higher yield and higher purity of the product.

In particular, it is found that when utilizing 4-bromo-2-methoxyimino-3-oxo butyric acid chloride (IV),

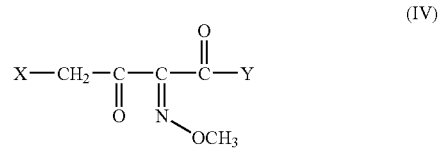

having a purity of at least 95%, preferably of 97-98% and containing di- and poly-brominated compounds less than 0.5% and prepared by the method disclosed in WO 03/045899 is utilized for reaction with (N,O)-bis trialkylsilyl 7-amino-3-[2,5-dihydro-6-hydroxy-2-methyl-5-oxo-as-triazin-3-yl]-3-cephem-4-carboxylic acid (III),

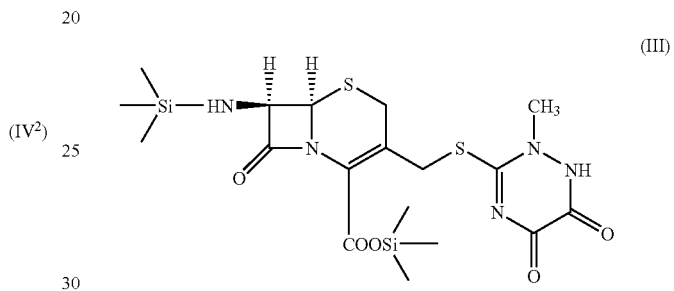

(a) the level of the starting compound (III) remaining unreacted is less than 1.0%, whereas when compound (IV), as prepared by any of the prior art methods, having a purity of ca. 87% and containing di- and poly-brominated compounds in the range of 2-3% is employed the level of the starting compound (III) remaining unreacted is higher and in the range of 4.0 to 6.0%.

(b) Further, when (6R,7R)-7-[[4-halo-2-(Z)-methoxyimino]acetamido]-3-[(2,5-dihydro-6-hydroxy-2-methyl-5-Ox0-as-triazin-3-yl)thio]methyl-3-cephem-4-carboxylic acid trialkylsilyl ester (V),

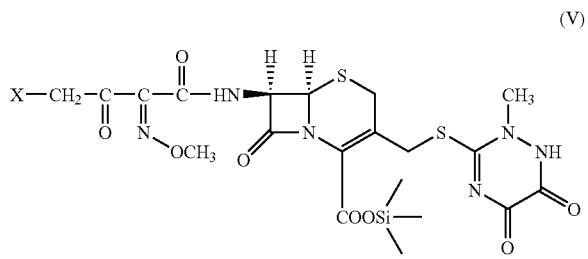

thus obtained by the two methods is converted to ceftriaxone (I) by reaction with thiourea and subsequently to ceftriaxone (II), better conversion, better quality and better color absorbance is obtained by the present method over that of prior art methods.

A comparison of the HPLC monitoring results of the synthesis of ceftriaxone (I) utilizing 4-bromo-2-methoxyimino-3-oxo-butyric acid chloride (IV) prepared as per the method of WO 03/045899 (having a purity of 97%, containing di-and poly-brominated compounds less than 0.50%) and that prepared as per the prior art methods (having a purity of ca. 87%, containing di- and poly-brominated compounds between 2-3%) is summarized in Table-I.

Another comparison of the yield, quality and color absorbance of ceftriaxone sodium (II) obtained utilizing 4-bromo-2-methoxyimino-3-oxo-butyric acid chloride (IV) prepared as per the method of WO 03/045899 (having a purity of 97% and containing di- and polybrominated compounds less than 0.5%) and that prepared as per the prior art methods (having a purity of ca. 87% and containing di- and poly-brominated compounds in the range of 2-3%) is summarized in Table-II.

TABLE I

Comparison of the HPLC monitoring results obtained in the reaction of (N,0)-bis trialkylsilyl 7-amino-3-[2,5-dihydro-6-hydroxy-2-methyl-5-oxo-as-triazin-3 yl]-3-cephem-4-carboxylic acid (III) with 4-bromo-2-methoxyimino-3-oxo butyric acid chloride (IV) prepared by any of the prior art methods, and as prepared by the method disclosed in WO 03/045899 in the synthesis of ceftriaxone (I)

| | | HPLC Monitoring Results* | | | |
|---|---|---|---|---|---|
| | | Preparation of Compound (V) | | Preparation of ceftriaxone (I) | |
| Sr. No. | Source of compound purity (%) | yo Compound (III) unreacted | % Compound (V) formed | Yo Compound (VI) unreacted | % Ceftriaxone (I) formed |
| | Prepared as per prior art methods (Ca. 87%) | 4.50 | 80.25 | 2.70 | 85.46 |
| 02 | Prepared as per prior art methods (Ca. 87%) | 6.33 | 78.64 | 1.40 | 81.86 |
| 03 | Prepared as per the method of WO 031045899 (Ca. 97%) | 0.42 | 92.56 | 0.01 | 88.03 |
| 04 | Prepared as per the method of WO 031045899 (Ca. 97%) | 0.86 | 90.93 | 0.35 | 87.37 |

*Reactions carried out under identical conditions and monitored under identical HPLC conditions

TABLE II

Yield, quality, level of impurities, color absorbance etc. of ceftriaxone (I) and ceftriaxone sodium (II) obtained utilizing 4-bromo-2-methoxyimino-3-oxo buyric acid chloride (IV) prepared by any of the prior art methods, and as prepared by the method disclosed in WO 03/045899

| Sr. No. | Details | Using 4-bromo-2-methoxyimino-3-oxo butyric acid chloride (IV) prepared by any of the prior art method (Purity ca. 87%) | Using 4-bromo-2 methoxyimino-3-oxo butyric acid chloride prepared by the method disclosed in WO 031045899 (Purity ca. 97%) |
|---|---|---|---|
| 01 | Yield of ceftriaxone sodium (II); % w/w | 0.80 | 0.88 |
| 02 | Yield of ceftriaxone sodium (II); % molar | 45.30 | 49.40 |
| 03 | Assay of ceftriaxone sodium (II) | 90.00 | 94.00 |
| 04 | % Total Impurities | 0.50 | 0.15 |
| 05 | color absorbance of ceftriaxone sodium (II) | | |

* Reactions carried out under identical conditions

The 4-halo-2-methoxyimino-3-oxo-butyric acid halide of formula (IV), as mentioned hereinearlier is prepared in situ and reacted with the silyl derivative (III). Compound (IV) is typically employed in slight excess of molar proportions of 1.0 moles per mole of compound (III), and can be employed in molar proportions of 1.1 to 1.5 moles per mole of compound of formula (III).

2. Effect of Utilization of an Acid Scavenging Agent

In the course of the reaction of the 4-halo-2-methoxyimino-3-oxo-butyric acid chloride (IV) with (N,O)-bis trialkylsilyl 7-amino-3-[2,5-dihydro-6-hydroxy-2-methyl-5-oxo-astriazin-3-yl]-3-cephem-4-carboxylic acid (III) to give (6R,7R)-7-[[4-halo-2-(Z)-methoxyimino]acetamido]-3-[(2, 5-dihydro-6-hydroxy-2-methyl-5-oxo-as-triazin-3-yl)thio]methyl-3-cephem-4-carboxylic acid trialkylsilyl ester (V), hydrogen halide is generated, which can lead to incomplete reaction or lead to formation of impurities.

The present inventors have found that effective neutralisation or trapping of hydrogen halide formed during the reaction could be achieved through addition of an acid scavenging agent, which importantly does not take part or interfere in the essential reaction but greatly enhances the efficiency of the reaction.

Any compound or substance capable of neutralizing or trapping the hydrogen halide formed in the reaction can be employed. These include both organic and inorganic acid scavengers selected from ethylene oxide, propylene oxide, butylene oxide, acetamide, epichlohydrin, calcium oxide, disodium hydrogen phosphate, calcium carbonate, quartemary ammonium phosphates, etc. However, those reagents which are soluble in the particular inert water-immiscible organic solvent employed for the reaction are preferred. The most preferred acid scavenging agent is acetamide.

Typically, the acid scavenging agent is employed in molar proportions to the 7-aminocephalosporonic acid derivative (III). In particular, it is employed in proportions of 1.0 to 3.0 moles per mole of the 7-amino-cephalosporonic acid derivative (III) and preferably in proportions of 1.0 to 1.5 moles per mole of the 7-amino-cephalosporonic acid derivative (III).

The inert water-immiscible organic solvents that can be employed in the process are those, which apart from their non-participation in the essential reaction are able to form a two-phase system with water. Such a solvent offers advantage in effecting hydrolysis of the 4-trialkyl ester group of the 4-carboxylic acid function of compound (V) formed in the reaction, without its isolation in the next stage of the one-pot process of the present invention.

Suitable inert water-immiscible organic solvents that can be employed include halogenated e.g. chlorinated hydrocarbons, e.g. dichloromethane; esters e.g. acetic acid $(C_{1-4})$ alkyl esters e.g. ethyl acetate; ethers e.g. diisopropylether etc. Chlorinated hydrocarbons are preferred and amongst these dichloromethane is the most preferred.

Addition of the acid scavenging agent is found to keep the level of the starting compound (III) remaining unreacted is less than 1.0%, whereas in the absence of an acid binding agent the amount of starting amount remaining unreacted is in the range of 3-5%. Further, when (6R,7R)-7-[[4-halo-2-(Z)-methoxyimino]acetamido]-3-[(2,5-dihydro-6-hydroxy-2-methyl-5-oxo-as-triazin-3-yl)thio]methyl-3-cephem-4-carboxylic acid trialkylsilyl ester (V), thus obtained by the two methods is converted to ceftriaxone (I) by reaction with thiourea, better conversion is obtained in the method wherein an acid scavenging agent has been added.

A comparison of the HPLC monitoring results of the synthesis of ceftriaxone (I) utilizing 4-bromo-2-methoxyimino-3-oxo-butyric acid chloride (IV) prepared as per the method of WO 03/045899 (having a purity of 97% and containing di- and poly-brominated compounds less than 0.5%) in the absence and presence of an acid scavenging agent is summarized in Table-III.

Another comparison of the yield, quality and color absorbance of ceftriaxone sodium (II) obtained utilizing 4-bromo-2-methoxyimino-3-oxo-butyric acid chloride (IV) prepared as per the method of WO 03/045899 (having a purity of 97% and containing di- and poly-brominated compounds less than 0.5%) and that prepared as per the prior art methods (having a purity of ca. 87% and containing di- and poly-brominated compounds in the range of 4-5%) in the presence of an acid scavenging agent is summarized in Table-IV.

In an embodiment of the invention, to a solution of (N,O)-bis trialkylsilyl 7-amino-3-[2,5-dihydro-6-hydroxy-2-methyl-5-oxo-as-triazin-3-yl]-3-cephem-4-carboxylic acid (III) in the inert water-immiscible organic solvent cooled to −40° C. to −60° C. is added the acid scavenging agent. To this is added a solution of 4-halo-2-methoxyimino-3-oxo-butyryl chloride (IV) in the inert water-immiscible organic solvent, in turn cooled to −40° C. to −60° C. over a period of 5 to 10 minutes. The reaction mixture is agitated at −20° C. to −30° C. for 30 minutes to 1 hour under an inert gas atmosphere till completion of reaction. The solution of (6R,7R)-7-[[4-halo-2-(Z)-methoxyimino]acetamido]-3-[(2,5-dihydro-6-hydroxy-2-methyl-5-oxo-as-triazin-3-yl)thio]methyl-3-cephem-4-carboxylic acid trialkylsilyl ester (V), in the inert water-immiscible organic solvent thus obtained, is used as such without isolation of the product for the next hydrolysis step.

TABLE III

Comparison of the HPLC monitoring results obtained in the reaction of (N,O)-bis trialkylsilyl 7-amino-3-[2,5-dihydro-6-hydroxy-2-methyl-5-oxo-as-triazin-3 yl]-3-cephem-4-carboxylic acid (III) with 4-bromo-2-methoxyimino-3-oxo butyric acid chloride (IV) prepared by the method disclosed in WO 03/045899 in the presence and absence of an acid scavenging agent for synthesis of ceftriaxone (I)

| | | HPLC Monitoring Results* | | | |
|---|---|---|---|---|---|
| | | Preparation of Compound (V) | | Preparation of ceftriaxone (I) | |
| Sr. No. | Acid Scavenging Agent added | % Compound (III) unreacted | % Compound (V) formed | % Compound (VI) unreacted | % Ceftriaxone (I) formed |
| 01 | None | 3.76 | 87.89 | 1.70 | 84.00 |
| 02 | None | 4.70 | 86.15 | 0.49 | 84.00 |

TABLE III-continued

Comparison of the HPLC monitoring results obtained in the reaction of (N,O)-bis trialkylsilyl 7-amino-3-[2,5-dihydro-6-hydroxy-2-methyl-5-oxo-as-triazin-3 yl]-3-cephem-4-carboxylic acid (III) with 4-bromo-2-methoxyimino-3-oxo butyric acid chloride (IV) prepared by the method disclosed in WO 03/045899 in the presence and absence of an acid scavenging agent for synthesis of ceftriaxone (I)

| | | HPLC Monitoring Results* | | | |
|---|---|---|---|---|---|
| | | Preparation of Compound (V) | | Preparation of ceftriaxone (I) | |
| Sr. No. | Acid Scavenging Agent added | % Compound (III) unreacted | % Compound (V) formed | % Compound (VI) unreacted | % Ceftriaxone (I) formed |
| 03 | Acetamide | 0.42 | 92.56 | 0.01 | 88.03 |
| 04 | Acetamide | 0.86 | 90.93 | 0.35 | 87.37 |

*Reactions carried out under identical conditions and monitored under identical HPLC conditions The starting (N,O)-bis trialkylsilyl 7-amino-3-[2,5-dihydro-6-hydroxy-2-methyl-5-oxo-as-triazin-3-yl]-3-cephem-4-carboxylic acid (III) can be prepared as per methods known in the art comprising silylation of 7-amino-3-[2,5-dihydro-6-hydroxy-2-methyl-5-oxo-as-triazin-3-yl]-3-cephem-4-carboxylic acid with a silylating agent in an inert water-immiscible organic solvent.

Appropriate silylating agents include e.g. silylated amides; such as N,O-bis-(trimethylsilyl)acetamide (BSA), Bis-silyl urea (BSU) or a mixture of hexamethyl disilazane (HMDS) and trimethylchlorosilane (TMCS).

Suitable inert water-immiscible organic solvents for effecting the silylation include those mentioned hereinearlier include halogenated e.g. chlorinated hydrocarbons, e.g. dichloromethane; esters e.g. acetic acid ($C_{1-4}$) alkyl esters e.g. ethyl acetate; ethers e.g. diisopropylether etc. Chlorinated hydrocarbons are preferred and amongst these dichloromethane is the most preferred.

TABLE IV

Yield, quality, level of impurities, color absorbance etc. of ceftriaxone (I) and ceftriaxone sodium (II) obtained utilizing 4-bromo-2-methoxyimino-3-oxo butyric acid chloride (IV) prepared by any of the prior art methods, and as prepared by the method disclosed in WO 031045899 in thepresence of an acid scavenging agent, viz. acetamide

| Sr. No. | Details | Using 4-bromo-2-methoxyimino-3-oxo butyric acid chloride (IV) prepared by any of the prior art methods in the presence of acetamide | Using 4-bromo-2 methoxyimino-3-oxo butyric acid chloride prepared by the method disclosed in WO 031045899 in the presence of acetamide |
|---|---|---|---|
| 01 | Yield of ceftriaxone sodium (II); % w/w | 0.88 | 0.98 |
| 02 | Yield of ceftriaxone sodium (II); % molar | 49.41 | 54.87 |
| 03 | Assay of ceftriaxone sodium (II) | 93.00 | 94.00 |
| 04 | % Total Impurities | 0.10 | 0.06 |
| 05 | color absorbance of ceftriaxone sodium (II) | 0.08 | 0.04 |

* Reactions carried out under identical conditions

Typically, 7-amino-3-[2,5-dihydro-6-hydroxy-2-methyl-5-oxo-as-triazin-3-yl]-3-cephem-4-carboxylic acid is dissolved in the appropriate inert water-immiscible organic solvent and water is azeotropically removed from the solution. To this added the silylating agent and the mixture heated or refluxed till silylation is complete. The solution of (N,O)-bis trialkylsilyl 7-amino-3-[2,5-dihydro-6-hydroxy-2-methyl-5-oxo-as-triazin-3-yl]-3-cephem-4-carboxylic acid (III), thus produced is cooled to −40° C. to −60° C. under an inert gas atmosphere for reaction with compound (IV).

The other starting compound, viz. 4-halo-2-methoxyimino-3-oxo-butyric acid halide (IV), specially 4-bromo-2-methoxyimino-3-oxo-butyric acid halide as mentioned hereinbefore is prepared as per the method disclosed in WO 03/045899.

The method comprises bromination of tert-butyl-2-methoxyimino-3-oxo-butyrate in an inert organic solvent in the presence of a $C_{1-4}$ alcohol and acetyl bromide at −15° C. to +15° C., followed by crystallization to give the compound having purity of at least 95% and containing di- and polybrominated compounds less than 0.5%.

3. Effect of the Water-Miscible Organic Solvent in the Hydrolysis of the Trialkylsilyl Ester and the Utilization of an Alkali Metal Containing Inorganic Base and pH in the Step of Formation of Ceftriaxone The hydrolysis of the trialkylsilyl ester group of the 4-carboxylic acid function of the product obtained in the previous step i.e. hydrolysis of (6R,7R)-7-[[4-halo-2-(Z)-methoxyimino acetamido]-3-[(2,5-dihydro-6-hydroxy-2-methyl-5-oxo-as-triazin-3-yl)thio]methyl-3-cephem-4-carboxylic acid trialkylsilyl ester (V) to the corresponding free carboxylic acid compound, viz. (6R,7R)-7-[[4-halo-2-(Z)-methoxyimino]acetamido]-3-[(2,5-dihydro-6-hydroxy-2-methyl-5-oxo-as-triazin-3-yl)thio]methyl-3-cephem-4-carboxylic acid (VI) can be performed by methods known in the art.

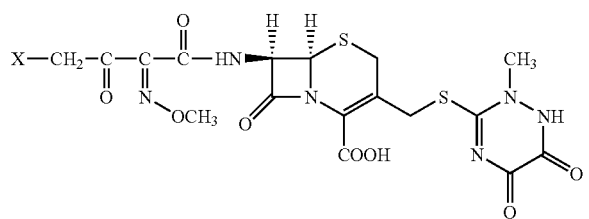
(VI)

However, in the present invention it has been found that the same could be achieved advantageously if the hydrolysis is effected by adding the solution of (6R,7R)-7-[[4-halo-2-(Z)-methoxyimino]acetamido]-3-[(2,5-dihydro-6-hydroxy-2-methyl-5-oxo-as-triazin-3-yl)thio]methyl-3-cephem-4-carboxylic acid trialkylsilyl ester (V) in the inert water-immiscible organic solvent to a 1:1 mixture of water and water-miscible organic solvent or vice versa. The advantage is that the hydrolysed product, viz. (6R,7R)-7-[[4-halo-2-(Z)-methoxyimino]acetamido]-3-[(2,5-dihydro-6-hydroxy-2-methyl-5-oxo-as-triazin-3-yl)thio]methyl-3-cephem-4-carboxylic acid (VI) gets selectively partitioned in the organic phase and can be separated from the aqueous phase and without isolation the solution containing the same can be used for further conversion to ceftriaxone, Any water-miscible organic solvent can be employed in admixture with water for the hydrolysis step. However, it is advantageous to employ water-miscible organic solvents that have some solubility in the inert water-immiscible organic solvent used, since the amount of such water-miscible organic solvents present in the solution of (6R,7R)-7-[[4-halo-2-(Z)-methoxyimino]acetamido]-3-[(2,5-dihydro-6-hydroxy-2-methyl-5-oxo-as-triazin-3-yl]methyl-3-cephem-4-carboxylic acid (VI) in the inert water-immiscible organic solvent prevents precipitation of ceftriaxone from the reaction mixture during its reaction with thiourea in the next step.

Suitable water-miscible organic solvents that can be employed advantageously in the hydrolysis step are selected from tetrahydrofixan and acetonitrile. Of these, tetrahydrofuran is the preferred water-miscible organic solvent.

Typically, after the reaction of 4-halo-2-methoxyimino-3-oxo butyric acid chloride (IV), prepared as per the method disclosed in WO 03/045899 with (N,O)-bis trialkylsilyl 7-amino-3-[2,5-dihydro-6-hydroxy-2-methyl-5-oxo-as-triazin-3-yl]-3-cephem-4-carboxylic acid (III) in an inert water-immiscible organic solvent in the presence of the acid scavenging agent the reaction mixture containing (6R,7R)-7-[[4-halo-2-(Z)-methoxyimino]acetamido]-3-[(2,5-dihydro-6-hydroxy-2-methyl-5-oxo-as-triazin-3-yl)thio]methyl-3-cephem-4-carboxylic acid trialkylsilyl ester (V) thus produced is added to a 1:1 mixture of water and the water-miscible organic solvent, specified hereinabove at a temperature 10° C. to 15° C., and agitated well and the layers allowed to separate. The organic layer containing the (6R,7R)-7-[[4-halo-2-(Z)-methoxyimino]acetamido]-3-[(2,5-dihydro-6-hydroxy-2-methyl-5-oxo-as-triazin-3-yl)thio]methyl-3-cephem-4-carboxylic acid (VI) is separated, washed with water and kept for reaction with thiourea in the next step.

Alternatively, the step of hydrolysis could be achieved by addition of a mixture of water and the water-miscible organic solvent, specified hereinabove, cooled to a temperature 10° C. to 15° C. to the reaction mixture containing (6R,7R)-7-[[4-halo-2-(Z)-methoxyimino]acetamido]-3-[(2,5-dihydro-6-hydroxy-2-meth-5-oxo-as-triazin-3-yl)thio]methyl-3-cephem-4-carboxylic acid trialkylsilyl ester (V) and the mixture agitated well and the layers allowed to separate. The organic layer containing the (6R,7R)-7-[[4-halo-2-(Z)-methoxyimino]acetamido]-3-[(2,5-dihydro-6-hydroxy-2-methyl-5-oxo-as-triazin-3-yl)thio]methyl-3-cephem-4-carboxylic acid (VI) is separated, washed with water and kept for reaction with thiourea in the next step.

To the solution of the (6R,7R)-7-[[4-halo-2-(Z)-methoxyimino]acetamido]-3-[(2,5-dihydro-6-hydroxy-2-methyl-5-oxo-as-triazin-3-yl)thio]methyl-3-cephem-4-carboxylic acid (VI) in the inert water-immiscible organic solvent cooled to 0° C. to 5° C. is added a solution of thiourea in water and the mixture agitated at the same temperature for 45 mins to 60 nms. Thereafter, a solution of the alkali metal containing inorganic base in water is added maintaining a pH of 5.0-5.50 during the addition. Thereafter, the pH is maintained till completion of reaction, after which the aqueous phase containing the alkali metal salt of ceftriaxone of formula (II$^1$), wherein M is an alkali metal, substantially free of impurities is separated from the organic phase, which selectively takes away any unreacted starting material and other impurities formed during the reaction.

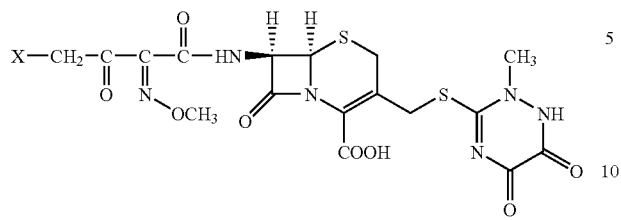

(VI)

Thiourea can be employed in molar proportions of 1.0 to 3.0 moles per mole of compound of formula (III), preferably in molar proportions of 1.0 to 1.5 moles per mole of compound of formula (III).

The advantage of forming a salt the 4-carboxylic acid function of ceftriaxone (I) with an alkali metal containing inorganic base is that such salts do not separate/precipitate out during reaction with thiourea unlike the salts formed with organic bases, specially triethylamine as would be evident from the description in Example-2 of U.S. Pat. No. 6,552,186 B2. This facilitates selective partitioning of impurities in the organic phase, leaving ceftriaxone in the form of alkali metal salt of formula (II'), in the aqueous phase, substantially free of impurities.

The alkali metal containing inorganic base is selected from hydroxides, carbonates and hydrogen carbonates of alkali metals and are selected from sodium hydroxide, potassium hydroxide, lithium hydroxide, sodium carbonate, potassium carbonate, lithium carbonates sodium hydrogen carbonate, potassium hydrogen carbonate, lithium hydrogen carbonate etc. Of these the hydroxides of alkali metals are preferred and of the hydroxides of alkali metals, sodium hydroxide is the most preferred alkali metal containing inorganic base.

The alkali metal containing inorganic base is employed in molar proportions of 2.0 to 5.0 moles per mole of compound of formula (III). Preferably, the alkali metal containing inorganic base is employed in molar proportions of 2.0 to 3.0 moles per mole of compound of formula (III).

The aqueous solution of the ceftriaxone alkali metal salt (III) thus obtained is mixed with a mixture of organic solvents selected from a water-miscible and a water-immiscible solvent and treated with an acid at a temperature of 20° C. to 25° C. till pH 3.80±0.2 is attained at which point the solution starts becoming turbid. The mixture is seeded with a crystal of ceftriaxone and the pH readjusted by addition of an acid to 2.50±0.20. The precipitated ceftriaxone (I) is filtered, washed with water and the water-miscible organic solvent and dried.

The entire operation is repeated once more, if necessary to give ceftriaxone of high purity. The water-miscible organic solvent is selected from those mentioned hereinbefore i.e. tetrahydrofuran and acetonitrile or selected from a $C_{1-4}$ lower alcohol such as methanol, ethanol, 1-propanol, 2-propanol etc.

The water-immiscible organic solvent is selected from chlorinated hydrocarbons e.g. dichloromethane; acetic acid ($C_{1-4}$) alkyl esters e.g. ethyl acetate; ethers e.g. diisopropylether etc.

An inorganic or organic acid can be employed for neutralisation of the salt (II[1]). Suitable inorganic acids can be selected from hydrochloric, sulfuric, and phosphoric acid. Suitable organic acids can be selected from formic, acetic, p-toluenesulfonic and methanesulfonic acid. Organic acids are preferred over inorganic acids and of the organic acids formic acid is the most preferred one.

4. Effect of pH on the Color Absorbance of Ceftriaxone Sodium Prepared

The ceftriaxone (I), thus produced is suspended in cold water. To the suspension is carefully added an organic base at 0° C. to 5° C. maintaining a pH of 5.4±0.2 to produce a solution of the amine salt of ceftriaxone in water of formula (VII), wherein Q is the organic base.

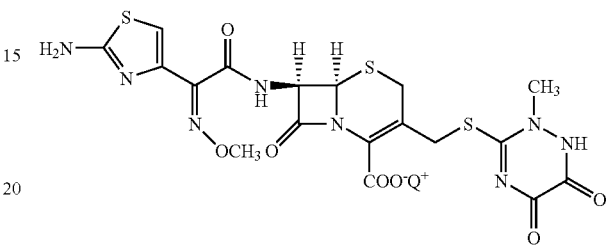

(VII)

It has been found that the pH at which ceftriaxone (I) is dissolved in water with the aid of the inorganic base is critical in determining the color absorbance of the final product i.e. ceftriaxone sodium (II). In the prior art methods, specially U.S. Pat. No. 6,552,186 B2, the pH at which ceftriaxone is dissolved is 6.50. However, at this pH the product obtained after formation of the salt with a sodium metal carrier i.e. ceftriaxone sodium is found to have higher color absorbance, which as mentioned hereinbefore is not suitable for formulation into a suitable dosage form.

The present inventors have found that a pH of 5.4±0.2 is the most optimum giving very low color absorbance to the product, thereby enhancing suitability of ceftriaxone sodium for suitable formulations.

The effect of pH on the color absorbance of ceftriaxone sodium produced is summarized in Table-V.

TABLE V

Effect of ph on the color absorbance of ceftriaxone sodium (II)

| pH of dissolution of ceftriaxone (I) in water with the aid of an organic base | color absorbance* of ceftriaxone sodium (II) obtained (in AU) |
|---|---|
| 7.80 | 0.096 |
| 7.30 | 0.093 |
| 6.45 | 0.089 |
| 6.20 | 0.069 |
| 5.45 | 0.058 |
| 5.40 | 0.050 |

*(12% solution in Water for Injection at 450 nm)

The color absorbance of the samples were determined using a Shimadzu, UV-visible spectrophotometer (Model UV-1700). In a typical method 1.2 gm of the test sample was taken in a 10 ml volumetric flask and the volume made-up with water for injection. The absorbance of the samples at 450 nm were recorded using water for injection as the blank standard.

The organic base employed for adjusting the pH for dissolution of ceftriaxone (I) in water can be selected from diethylamine, triethylamine, diisopropylamine, cyclohexylamine, pyridine, 2,4-dimethylamino pyridine, N-methyl morpholine etc. Triethylamine, because of its low cost is preferred.

The solution of the amine salt (VII), thus produced can be charcoalized and is mixed with a water-miscible organic solvent. To this is added a sodium metal carrier and the sodium exchange reaction effected to give ceftriaxone sodium (II) as the hemiheptahydrate.

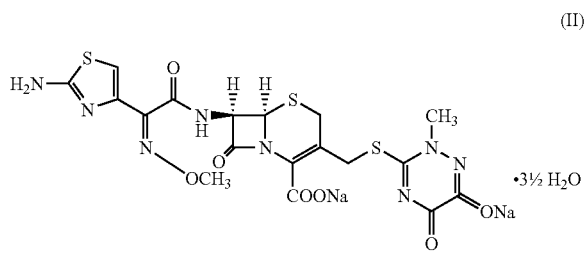

(II)

Suitable water-miscible organic solvents are those mentioned hereinbefore and also included ketonic solvents e.g. acetone.

Suitable alkali metal carriers can be selected from those routinely employed in the art e.g. sodium acetate and 2-ethyl sodium hexanoate, 2-ethyl sodium octanoate etc.

From the foregoing, it would be abundantly evident that the selection of the right quality of reactants, type of solvents, pH, other reaction conditions or parameters etc., as per the present invention provides an improved method for preparation of ceftriaxone (I) and its conversion to ceftriaxone sodium (II) in high yield, possessing high purity, high stability, low color value, thereby rendering it highly amenable for formulation into a suitable dosage form and for administration to human beings.

To summarize, the distinguishing features of the present invention and the contribution of all the abovementioned selections of the present invention vis-a-vis the methods described in the closest prior art, viz. Example-2 of U.S. Pat. No. 6,552,186 B2 in the manufacture of ceftriaxone sodium (II) in high yield, purity, and low color absorbance can be appreciated from the results given in Table-VI.

The invention is farther illustrated by the following examples, which in no way should be construed as to limiting the scope of the invention.

TABLE VI

The distinguishing features of the present invention vis-a-vis that of the method described in LISPatent No. 6,552,186 B2 for manufacture of ceftriaxone sodium (II).

| Sr. No. | Differences | Method described in U.S. Pat. No. 6,522,186 R2* | Method of Present Invention |
|---|---|---|---|
| 01 | Purity of 4-halo-2-methoxyimino-3-oxobutyric acid (III) used | No mention of purity | At least 95.00% |
| 02 | Di- and poly-bromo compounds present in the 4-halo-2-methoxyimino-3 oxobutyric acid (III) used | No mention | Less than 0.50% |
| 03 | Utilization of an acid scavenging agent in the reaction of Compound (III) and Compound (IV) | None | Yes |
| 04 | Solvent used in the reaction of Compound (III) and Compound (IV) | Inert water-immiscible organic solvent | Inert water-immiscible organic solvent |
| 05 | Base utilized in the reaction of Compound (VI) with thiourea | Organic base, forming a quarternary amime salt of ceftriaxone, which precipitates out from the reaction mixture | Alkali metal containing inorganic base, forming an alkali metal salt of ceftriaxone, which remains dissolved in the aqueous phase |
| 06 | pH at which the reaction of Compound (VI) with thiourea is carried out | No mention | 5.0 to 5.5 |
| 07 | pH at which formation of ceftriaxone sodium (II) is effected | 6.50 | 5.4 ± 0.20 |
| 08 | Overall yield of ceftriaxone sodium (II) from compound (III) [% Molar] | 64.0-65.0" | 56.0-58.0† |
| 09 | Purity of ceftriaxone sodium (II; %) | 73.0-79.0 | 93.0-94.0 |
| 10 | % of Total Impurities | 4.50-6.80 | 0.18-0.19 |
| 11 | color absorbance (AU) | 1.0-1.82 | 0.04-0.05 |
| 12 | Suitability for formulation into a dosage form | Highly unsuitable | Highly suitable |

*As per replication of Example-2 of this patent.
x 47.00 to 51.00% based on purity
†53.00 to 54% based on purity
} This means better specificity obtained from the present invention compared to prior art

REFERENCE EXAMPLE-1

Preparation of Ceftriaxone Sodium (II) as Per the Method Described in Example-2 of U.S. Pat. No. 6,552,186 B2

Step-1: Preparation of (N,O)-bis trialkylsilyl 7-amino-3-[2,5-dihydro-6-hydroxy-2-methyl5-oxo-as-triazin-3-yl]-3-cephem-4-carboxylic acid (III)

50 gm (0.135 moles) of 7-amino-3-{[(2,5-dihydro-6-hydroxy-2-methyl-5-oxo-as-triazin-3-yl)thio]methyl)}-3-cephem-4-carboxylic acid was suspended in dichloromethane (500 ml). An additional amount of 1000 ml of dichloromethane was added to the suspension and distilled out to effect azeotropic removal of water. To the suspension was added Bis silyl acetamide (109.70 gm; 0.540 moles) at 25° C. to 30° C. and the mixture agitated under an atmosphere of nitrogen for 2 hours. The solution of (N,O)-bis trialkylsilyl 7-amino-3-[2,5-dihydro-6-hydroxy-2-methyl-5-oxo-as-triazin-3-yl]-3-cephem-4-carboxylic acid (III) thus obtained was cooled to −10° C.

Step-2: Preparation of 4-bromo-2-methoxyimino-3-oxo Yutyric acid chloride (IV)

To a solution of 30.20 gm (0.154 moles) of 4-bromo-2-methoxyimino-3-oxo-butyric acid in dichloromethane (230 ml) cooled to −10° C. under an atmosphere of nitrogen was added phosphorous pentachloride (28.10 gm; 0.134 moles) in portions and the solution of 4-bromo-2-methoxyimino-3-oxo butyric acid chloride (IV) in dichloromethane thus obtained is kept cooled to −10° C.

Step-3: Preparation of (6R,7R)-7-[[4-halo-2-(Z)-methoxyimino]acetamido]-3-[(2,5-dihydro-6-hydroxy-2-methyl-5-oxo-as-triazin-3-yl)thio]methyl-3-cephem-4-carboxylic acid (VI) via (6R,7R)-7-[[4-halo-2-(Z)-methoxyimino]acetamido]-3-[(2,5-dihydro-6-hydroxy-2-methyl-5-oxo-as-triazin-3 yl)thio]methyl-3-cephem-4-carboxylic acid trialkysilyl ester (V)

The solution obtained in Step-1 was mixed with the solution obtained in Step-2 at −10° C. to 0° C. and the resulting reaction mixture containing (6R,7R)-7-[[4-halo-2-(Z)-methoxyimino]acetamido]-3-[(2,5-dihydro-6-hydroxy-2-methyl-5-oxo-as-triazin-3-yl)thio]methyl-3-cephem-4-carboxylic acid trialkylsilyl ester (V) thus formed was added to a mixture of sodium bicarbonate (56.54 gm), water (448 ml) and 2-propanol (448 ml). The pH the reaction mixture was adjusted to 2.0 with 2N hydrochloric acid. The organic phase containing (6R,7R)-7-[[4-halo-2-(Z)-methoxyimino]acetamido]-3-[(2,5-dihydro-6-hydroxy-2-methyl-5-oxo-as-triazin-3-yl)thio]methyl-3-cephem-4-carboxylic acid (VI).

Step-4: Preparation of Ceftriaxone (I)

The solution of (6R,7R)-7-[[4-halo-2-(Z)-methoxyimino]acetamido]-3-[(2,5-dihydro-6-hydroxy-2-methyl-5-oxo-as-triazin-3-yl)thio]methyl-3-cephem-4-carboxylic acid (VI) in dichloromethane obtained in Step 3 was treated with water (22 ml), triethylamine (12.0 gm; 0.118 moles) and thiourea (9.0 gm; 0.118 moles) and the mixture agitated for 6 hours. The precipitated ceftriaxone (I) was filtered, washed with 2-propanol (50 ml) and the wet material used as such for conversion to the sodium salt.

Step-5: Preparation of Ceftriaxone Sodium (II)

The wet ceftriaxone (I) from Step-4 was suspended in acetone (400 ml) and water (40 ml) and treated with a solution of sodium acetate (8.2 gm) in water (100 ml). The reaction mixture was agitated for 2 hours and the crystallized solid was filtered, washed with acetone (50 ml) and dried under vacuum to give 57.0 gm (57% yield) of ceftriaxone sodium (II), having the following characteristics.

| Purity | 73.0-79.0% |
|---|---|
| Water Content | 8.70-12.65% |
| color absorbance | 1.00-1.80 AU |
| Total Impurities | 4.50-6.80% |

EXAMPLE-2

Preparation of Ceftriaxone Sodium (II) as Per the Method of the Present Invention utilizing 4-halo-2-methoxyimino-3-oxo butyric acid (IV) Having a Purity of 87% in the Absence of an Acid Scavenger

Step-1: Preparation of (N,O)-bis trialkylsilyl 7-amino-3-[2,5-dihydro-6-hydroxy-2-methyl-5-oxo-as-triazin-3 yl]-3-cephem-4-carboxylic acid (III)

A suspension of 7-amino-3-{[(2,5-dihydro-6-hydroxy-2-methyl-5-oxo-as-triazin-3 yl)thio]methyl)}-3-cephem-4-carboxylic acid (100 gm; 0.270 moles) and dichloromethane (2700 ml) was heated to reflux and 2000 ml of dichloromethane was distilled out till moisture content of the reaction mixture is below 0.06%. The reaction mixture was cooled to room temperature. To this was added 74.0 gm (0.458 moles) of hexamethyldisilazane and trimethylchlorosilane (10.8 gm; 0.0095 moles) and the mixture refluxed for 8 hours. The solution containing (N,O)-bis trialkylsilyl 7-amino-3-[2,5-dihydro-6-hydroxy-2-methyl-5-oxo-as-triazin-3-yl]-3-cephem-4-carboxylic acid (III) was gradually cooled to room temperature and subsequently cooled to −55° C.

Step-2: Preparation of 4-bromo-2-methoxyimino-3-oxo butyric acid chloride (IV)

To a suspension of phosphorous pentachloride (64.91 gm; 0.3113 moles) in dichloromethane (250 ml), cooled to −20° C. was added a solution of 4-bromo-2-methoxyimino-3-oxo butyric acid (66.41 gm; 0.2965 moles; purity ca. 87%; containing 4-5% of di- and poly-brominated compounds) in dichloromethane (250 ml) over a period of 30 minutes at −20° C. to −5° C. The temperature was raised to 5 to 10° C. and the reaction mixture purged with nitrogen gas for one to two hours to expel out hydrogen chloride gas.

The solution containing 4-bromo-2-methoxyimino-3-oxo butyric acid chloride (IV) was cooled to −10° C.

Step-3: Preparation of (6R,7R)-7-[[4-halo-2-(Z)-methoxyimino]acetamido]-3-[(2,5-dihydro-6-hydroxy-2-methyl-5-oxo-as-triazin-3 yl)thio]methyl-3-cephem-4-carboxylic acid (VI) via (6R,7R)-7-"4-halo-2-(Z) methoxyimino]acetamidol-3-[(2,5-dihydro-6-hydroxy-2-methyl-5-oxo-as-triazin-3-yl)thio]methyl-3-cephem-4-carboxylic acid trialkylsilyl ester (V)

The dichloromethane solution obtained in Step-2 was added to the dichloromethane solution obtained in Step-1 over a period of 30-45 minutes at −55° C. to −30° C. The reaction mixture was thereafter agitated at −30° C. to −20° C. till completion of reaction to give a solution of (6R,7R)-7-[[4-halo-2-(Z)-methoxyimino]acetamido]-3-[(2,5-dihydro-6-hydroxy-2-methyl-5-oxo-as-triazin-3-yl)thio]methyl-3-cephem-4-carboxylic acid trialkylsilyl ester (V) in dichloromethane.

The above solution was added to a mixture of water (800 ml) and tetrahydrofuran (400 ml) cooled to 10° C. to 15° C. over a period of 20-30 minutes. The mixture was agitated at the same temperature for 30 minutes and allowed the layers to separate. The separated organic layer was washed with water (400 ml) to give a solution of (6R,7R)-7-[[4-halo-2-(Z)-methoxyimino]acetamido]-3-[(2,5-dihydro-6-hydroxy-2-methyl-5-oxo-as-triazin-3-yl)thio]methyl-3-cephem-4-carboxylic acid (VI) in dichloromethane.

Step-4: Preparation of Ceftriaxone (I)

To a mixture of the solution of dichloromethane obtained in Step-3 and water (1200 ml), cooled to 3° C. to 5° C. was added a solution of thiourea (24.58 gm; 0.404 moles) in water (200 ml) and the mixture agitated for 60 minutes at the same temperature. To the mixture was added a solution of sodium bicarbonate (60-70 gm) in water (600-700 ml) over a period of 60 minutes to achieve a pH of 5.50. Thereafter, the pH was maintained between 5.0 to 5.5 and the reaction mixture agitated for 120 minutes till completion of reaction. The organic layer was separated from the aqueous phase. The aqueous phase was charcoalized and the charcoal filtered off. To the filtrate was added ethyl acetate (500 ml) and 2-propanol (100 ml) in one lot and the solution cooled to 20-25° C. To the solution was added a solution of aqueous formic acid (70%) till turbidity develops at a pH of about 3.80. The mixture was seeded with crystals of ceftriaxone, stirred for 30-45 minutes. The pH was adjusted to 2.50 and cooled to 0-5° C. and agitated for 120 minutes. The crystallized solid was filtered.

The wet material was optionally redissolved in water with the aid of triethylamine and recrystallized as per the method outlined above to give ceftriaxone (I).

Step-5: Preparation of Ceftriaxone Sodium (II)

To water (600 ml) cooled to 0-5° C. was added the wet ceftriaxone obtained in Step-4. to the mixture was added triethylamine (36.42 gm; 0.360 moles) till a clear solution was obtained, maintaining a pH of 5.4±0.20. The solution was charcoalized and the charcoal filtered off. To the filtrate was added a mixture of water (100 ml) and acetone (100 ml), followed by addition of a solution of 2-ethyl sodium hexanoate (64.35 gm; 0.387 moles) in acetone (600 ml) over a period of 3-45 minutes at 0-5° C. Thereafter, the temperature was raised to 20±2° C. and the reaction mixture agitated at this temperature for 15-30 minutes. Acetone (1000 ml) was added till turbidity develops to the solution. Thereafter, further acetone (2500 ml) was added and the mixture agitated at 20±2° C. for 90-120 minutes. The mixture was cooled to 13-15° C., agitated for 60 minutes and the solid filtered, washed with acetone (400 ml) and dried under vacuum at 25° C. to give 80.83 gm (45.32%) of ceftriaxone sodium (II), possessing the following characteristics.

| | |
|---|---|
| Purity | 90.30% |
| Water Content | 10.42% |
| color absorbance | 0.23 AU |
| Total Impurities | 0.50% |

EXAMPLE-3

Preparation of Ceftriaxone Sodium (II) as Per the Method of the Present Invention Utilizing 4-halo-2-methoxyimino-3-oxo butyric acid (IV) Having a Purity of 97% and Prepared as the Method Disclosed in WO03/045899 in the Absence of an Acid Scavenger Step-1: Preparation of (N,O)-bis trialkylsilyl 7-amino-3-[2,5-dihydro-6-hydroxy-2-methyl-5-oxo-as-triazin-3 yl]-3-cephem-4-carboxylic acid (III)

A suspension of 7-amino-3-{[(2,5-dihydro-6-hydroxy-2-methyl-5-oxo-as-triazin-3-yl)thio]methyl)}-3-cephem-4-carboxylic acid (100 gm; 0.270 moles) and dichloromethane (2700 ml) was heated to reflux and 2000 ml of dichloromethane was distilled out till moisture content of the reaction mixture is below 0.06%. The reaction mixture was cooled to room temperature. To this was added 74.0 gm (0.458 moles) of hexamethyldisilazane and trimethylchlorosilane (10.8 gm; 0.0095 moles) and the mixture refluxed for 8 hours. The solution containing (N,O)-bis trialkylsilyl 7-amino-3-[2,5-dihydro-6-hydroxy-2-methyl-5-oxo-as-triazin-3-yl]-3-cephem-4-carboxylic acid (III) was gradually cooled to room temperature and subsequently cooled to -55° C.

Step-2: Preparation of 4-bromo-2-methoxyimino-3-oxo butyric acid chloride (IV)

To a suspension of phosphorous pentachloride (64.91 gm; 0.3113 moles) in dichloromethane (250 ml), cooled to −20° C. was added a solution of 4-bromo-2-methoxyimino-3-oxo butyric acid (66.41 gm; 0.2965 moles; purity ca. 97%; containing <0.5% of di- and poly-brominated compounds and prepared as per the method disclosed in WO 03/045899) in dichloromethane (250 ml) over a period of 30 minutes at −20° C. to −5° C. The temperature was raised to 5 to 10° C. and the reaction mixture purged with nitrogen gas for one to two hours to expel out hydrogen chloride gas. The solution containing 4-bromo-2-methoxyimino-3-oxo butyric acid chloride (IV) was cooled to −10° C.

Step-3: Preparation of (6R,7R)-7-[[4-halo-2-(Z)-methoxyimino]acetamido]-3-[(2,5-dihydro-6-hydroxy-2-methyl-5-oxo-as-triazin-3 yl)thio]methyl-3-cephem-4-carboxylic acid (VI) via (6R,7R)-7-[[4-halo-2-(Z)-methoxyimino]acetamido]-3-[(2,5-dihydro-6-hydroxy-2-methyl-5-oxo-as-triazin-3 yl)thio]methyl-3-cephem-4-carboxylic acid trialkylsilyl ester (V)

The dichloromethane solution obtained in Step-2 was added to the dichloromethane solution obtained in Step-1 over a period of 30-45 minutes at −55° C. to 30° C. The reaction mixture was thereafter agitated at −30° C. to −20° C. till completion of reaction to give a solution of (6R,7R)-7-[[4-halo-2-(Z)-methoxyimino]acetamido]-3-[(2,5-dihydro-6-hydroxy-2-methyl-5-oxo-as-triazin-3-yl)thio]methyl-3-cephem-4-carboxylic acid trialkylsilyl ester (V) in dichloromethane.

The above solution was added to a mixture of water (800 ml) and tetrahydrofuran (400 ml) cooled to 10° C. to 15° C. over a period of 20-30 minutes. The mixture was agitated at the same temperature for 30 minutes and allowed the layers to separate. The separated organic layer was washed with water (400 ml) to give a solution of (6R,7R)-7-[[4-halo-2-(Z)-methoxyimino]acetamido]-3-[(2,5-dihydro-6-hydroxy-2-methyl-5-oxo-as-triazin-3-yl)thio]methyl-3-cephem-4-carboxylic acid (VI) in dichloromethane. Step-4: Preparation of Ceftriaxone (I)

To a mixture of the solution of dichloromethane obtained in Step-3 and water (1200 ml), cooled to 3° C. to 5° C. was added a solution of thiourea (24.58 gm; 0.404 moles) in water (200 ml) and the mixture agitated for 60 minutes at the same temperature. To the mixture was added a solution of sodium bicarbonate (60-70 gm) in water (600-700 ml) over a period of 60 minutes to achieve a pH of 5.50. Thereafter, the pH was maintained between 5.0 to 5.5 and the reaction mixture agitated for 120 minutes till completion of reaction. The organic layer was separated from the aqueous phase. The aqueous phase was charcoalized and the charcoal filtered off. To the filtrate was added ethyl acetate (500 ml) and 2-propanol (100 ml) in one lot and the solution cooled to 20-25° C. To the solution was added a solution of aqueous formic acid (70%) till turbidity develops at a pH of about 3.80. The mixture was seeded with crystals of ceftriaxone, stirred for 30-45 minutes. The pH was adjusted to 2.50 and cooled to 0-5° C. and agitated for 120 minutes. The crystallized solid was filtered.

The wet material was optionally redissolved in water with the aid of triethylamine and recrystallized as per the method outlined above to give ceftriaxone (I).

Step-5: Preparation of Ceftriaxone Sodium (II)

To water (600 ml) cooled to 0-5° C. was added the wet ceftriaxone obtained in Step-4. to the mixture was added triethylamine (36.42 gm; 0.360 moles) till a clear solution was obtained, maintaining a pH of 5.4 ±0.20. The solution was charcoalized and the charcoal filtered off. To the filtrate was added a mixture of water (100 ml) and acetone (100 ml), followed by addition of a solution of 2-ethyl sodium hexanoate (64.35 gm; 0.387 moles) in acetone (600 ml) over a period of 3-45 minutes at 0-5° C. Thereafter, the temperature was raised to 20±2° C. and the reaction mixture agitated at this temperature for 15-30 minutes. Acetone (1000 ml) was added till turbidity develops to the solution. Thereafter, further acetone (2500 ml) was added and the mixture agitated at 20±2° C. for 90-120 minutes. The mixture was cooled to 13-15° C., agitated for 60 minutes and the solid filtered, washed with acetone (400 ml) and dried under vacuum at 25° C. to give 87.07 gm (48.83%) of ceftriaxone sodium (II), possessing the following characteristics.

| Purity | 92.70% |
| Water Content | 92.28% |
| color absorbance | 0.08 AU |
| Total Impurities | 0.35% |

EXAMPLE-4

Preparation of Ceftriaxone Sodium (II) as per the Method of the Present Invention Utilizing 4-halo-2-methoxyimino-3-oxo butyric acid (IV) Having a Purity of 87% and in the Presence of an Acid Scavenger Step-1: Preparation of N, O)-his trialkylsilyl 7-amino-3-[2,5-dihydro-6-hydroxy-2-methyl-5-oxo-as-triazin-3 yl]-3-cephem-4-carboxylic acid (III)

A suspension of 7-amino-3-{[(2,5-dihydro-6-hydroxy-2-methyl-5-oxo-as-triazin-3yl)thio]methyl)}-3-cephem-4-carboxylic acid(100 gm; 0.270 moles) and dichloromethane (2700 ml) was heated to reflux and 2000 ml of dichloromethane was distilled out till moisture content of the reaction mixture is below 0.06%. The reaction mixture was cooled to room temperature. To this was added 74.0 gm (0.458 moles) of hexamethyldisilazane and trimethylchlorosilane (10.8 gm; 0.0095 moles) and the mixture refluxed for 8 hours. The solution containing (N,O)-bis trialkylsilyl 7-amino-3-[2,5-dihydro-6-hydroxy-2-methyl-5-oxo-as-triazin-3-yl]-3-cephem-4-carboxylic acid (III) was gradually cooled to room temperature. To the solution was added acetamide (23.85 gm; 0.4043 gi) and the mixture subsequently cooled to −55° C.

Step-2: Preparation of 4-bromo-2-methoxyimino-3-oxo butyric acid chloride (IV)

To a suspension of phosphorous pentachloride (64.91 gm; 0.3113 moles) in dichloromethane (250 ml), cooled to −20° C. was added a solution of 4-bromo-2-methoxyimino-3-oxo butyric acid (66.41 gm; 0.2965 moles; purity ca. 87%; containing 4-5% of di- and poly-brominated compounds) in dichloromethane (250 ml) over a period of 30 minutes at −20° C. to -5° C. The temperature was raised to 5 to 10° C. and the reaction mixture purged with nitrogen gas for one to two hours to expel out hydrogen chloride gas. The solution containing 4-bromo-2-methoxyimino-3-oxo butyric acid chloride (IV) was cooled to −10° C.

Step-3: Preparation of (6R,7R)-7-"4-halo-2(7)-methoxyimino]acetamido]-3-[(2,5-dihydro-6-hydroxy-2-methyl-5-oxo-as-triazin-3 yl)thio]methyl-3-cephem-4-carboxylic acid (VI) via (6R,7R)-7-[[4-halo-2-(Z)-methoxyimino]acetamido]-3-[(2,5-dihydro-6-hydroxy-2-methyl-5-oxo-as-triazin-3 yl)thio]methyl-3-cephem-4-carboxylic acid trialkylsilyl ester (V)

The dichloromethane solution obtained in Step-2 was added to the dichloromethane solution obtained in Step-1 over a period of 30-45 minutes at −55° C. to −30° C. The reaction mixture was thereafter agitated at −30° C. to −20° C. till completion of reaction to give a solution of (6R,7R)-7-[[4-halo-2-(Z)-methoxyimino]acetamido]-3-[(2,5-dihydro-6-hydroxy-2-methyl-5-oxo-as-triazin-3-yl)thio]methyl-3-cephem-4-carboxylic acid trialkylsilyl ester (V) in dichloromethane.

The above solution was added to a mixture of water (800 ml) and tetrahydrofuran (400 ml) cooled to 10° C. to 15° C. over a period of 20-30 minutes. The mixture was agitated at the same temperature for 30 minutes and allowed the layers to separate. The separated organic layer was washed with water (400 ml) to give a solution of (6R,7R)-7-[[4-halo-2-(Z)-methoxyimino]acetamido]-3-[(2,5-dihydro-6-hydroxy-2-methyl-5-oxo-as-triazin-3-yl)thio]methyl-3-cephem-4-carboxylic acid (VI) in dichloromethane.

Step-4: Preparation of Ceftriaxone (I)

To a mixture of the solution of dichloromethane obtained in Step-3 and water (1200 ml), cooled to 3° C. to 5° C. was added a solution of thiourea (24.58 gm; 0.404 moles) in water (200 ml) and the mixture agitated for 60 minutes at the same temperature. To the mixture was added a solution of sodium bicarbonate (60-70 gm) in water (600-700 ml) over a period of 60 minutes to achieve a pH of 5.50. Thereafter, the pH was maintained between 5.0 to 5.5 and the reaction mixture agitated for 120 minutes till completion of reaction. The organic layer was separated from the aqueous phase. The aqueous phase was charcoalized and the charcoal filtered off. To the filtrate was added ethyl acetate (500 ml) and 2-propanol (100 ml) in one lot and the solution cooled to 20-25° C. To the solution was added a solution of aqueous formic acid (70%) till turbidity develops at a pH of about 3.80. The mixture was seeded with crystals of ceftriaxone, stirred for 30-45 minutes. The pH was adjusted to 2.50 and cooled to 0-5° C. and agitated for 120 minutes. The crystallized solid was filtered.

The wet material was optionally redissolved in water with the aid of triethylamine and recrystallized as per the method outlined above to give ceftriaxone (I).

Step-5: Preparation of Ceftriaxone Sodium (II)

To water (600 ml) cooled to 0-5° C. was added the wet ceftriaxone obtained in Step-4. to the mixture was added triethylamine (36.42 gm; 0.360 moles) till a clear solution was obtained, maintaining a pH of 5.4±0.20. The solution was charcoalized and the charcoal filtered off. To the filtrate was added a mixture of water (100 ml) and acetone (100 ml), followed by addition of a solution of 2-ethyl sodium hexanoate (64.35 gm; 0.387 moles) in acetone (600 ml) over a period of 3-45 minutes at 0-5° C. Thereafter, the temperature was raised to 20±2° C. and the reaction mixture agitated at this temperature for 15-30 minutes. Acetone (1000 ml) was added till turbidity develops to the solution. Thereafter, further acetone (2500 ml) was added and the mixture agitated at 20±2° C. for 90-120 minutes. The mixture was cooled to 13-15° C., agitated for 60 minutes and the solid filtered, washed with acetone (400 ml) and dried under vacuum at 25° C. to give 88.12 gm (49.41%) of ceftriaxone sodium (II), possessing the following characteristics.

| | |
|---|---|
| Purity | 93.78% |
| Water Content | 10.23% |
| color absorbance | 0.08 AU |
| Total Impurities | 0.0.10% |

EXAMPLE-5

Preparation of Ceftriaxone Sodium (II) as per the Preferred Embodiment of the Present Invention Utilizing 4-halo-2-methoxyimino-3-oxo butyric acid (IV) Having a Purity of 97% and Prepared as the Method Disclosed in WO 03/045899 in the presence of an acid scavenger Step-1: Preparation of t(N,O)-bis trialkylsilyl 7-amino-3-[5-dihydro-6-hydroxy-2-methyl-5-oxo-as-triazin-3-yl]-3-cephem-4-carboxylic aid (III)

A suspension of 7-amino-3-{[(2,5-dihydro-6-hydroxy-2-methyl-5-oxo-as-triazin-3-yl)thio]methyl)}-3-cephem-4-carboxylic acid(100 gm; 0.270 moles) and dichloromethane (2700 ml) was heated to reflux and 2000 ml of dichloromethane was distilled out till moisture content of the reaction mixture is below 0.06%. The reaction mixture was cooled to room temperature. To this was added 74.0 gm (0.458 moles) of hexamethyldisilazane and trimethylchlorosilane (10.8 gm; 0.0095 moles) and the mixture refluxed for 8 hours. The solution containing (N,O)-bis trialkylsilyl 7-amino-3-[2,5-dihydro-6-hydroxy-2-methyl-5-oxo-as-triazin-3-yl]-3-cephem-4-carboxylic acid (III) was gradually cooled to room temperature. To the solution was added acetamide (23.85 gm; 0.4043 gm) and the mixture subsequently cooled to −55° C.

Step-2: Preparation of 4-bromo-2-methoxyimino-3-oxo butyric acid chloride (IV)

To a suspension of phosphorous pentachloride (64.91 gm; 0.3113 moles) in dichloromethane (250 ml), cooled to −20° C. was added a solution of 4-bromo-2-methoxyimino-3-oxo butyric acid (66.41 gm; 0.2965 moles; purity ca. 97%; containing<0.5% of di- and poly-brominated compounds and prepared as per the method disclosed in WO 03/045899) in dichloromethane (250 ml) over a period of 30 minutes at −20° C. to −5° C. The temperature was raised to 5 to 10° C. and the reaction mixture purged with nitrogen gas for one to two hours to expel out hydrogen chloride gas. The solution containing 4-bromo-2-methoxyimino-3-oxo butyric acid chloride (IV) was cooled to −10° C.

Step-3: Preparation of (6R,7R)-7-[[4-halo-2-(Z)-methoxyimino]acetamido]-3-[(2,5-dihydro-6-hydroxy-2-methyl-5-oxo-as-triazin-3-yl)thio]methyl-3-cephem-4-carboxylic acid (VI) via (6R,7R)-7-[[4-halo-2-(Z)-methoxyimino]acetamido]-3-[f(2,-dihydro-6-hydroxy-2-methyl-5-oxo-as-triazin-3-yl)thio]methyl-3-cephem-4-carboxylic acid trialkylsilyl ester (V)

The dichloromethane solution obtained in Step-2 was added to the dichloromethane solution obtained in Step-1 over a period of 30-45 minutes at −55° C. to −30° C. The reaction mixture was thereafter agitated at −30° C. to −20° C. till completion of reaction to give a solution of (6R,7R)-7-[[4-halo-2-(Z)-methoxyimino]acetamido]-3-[(2,5-dihydro-6hydroxy-2-methyl-5-oxo-as-triazin-3-yl)thio]methyl-3-cephem-4-carboxylic acid trialkylsilyl ester (V) in dichloromethane.

The above solution was added to a mixture of water (800 ml) and tetrahydrofuran (400 ml) cooled to 10° C. to 15° C. over a period of 20-30 minutes. The mixture was agitated at the same temperature for 30 minutes and allowed the layers to separate. The separated organic layer was washed with water (400 ml) to give a solution of (6R,7R)-7-[[4-halo-2-(Z)-methoxyimino]acetamido]-3-[(2,5-dihydro-6-hydroxy-2-methyl-5-oxo-as-triazin-3-yl)thio]methyl-3-cephem-4-carboxylic acid (VI) in dichloromethane.

Step-4: Preparation of Ceftriaxone (I)

To a mixture of the solution of dichloromethane obtained in Step-3 and water (1200 ml), cooled to 3° C. to 5° C. was added a solution of thiourea (24.58 gm; 0.404 moles) in water (200 ml) and the mixture agitated for 60 minutes at the same temperature. To the mixture was added a solution of sodium bicarbonate (60-70 gm) in water (600-700 ml) over a period of 60 minutes to achieve a pH of 5.50. Thereafter, the pH was maintained between 5.0 to 5.5 and the reaction mixture agitated for 120 minutes till completion of reaction. The organic layer was separated from the aqueous phase. The aqueous phase was charcoalized and the charcoal filtered off. To the filtrate was added ethyl acetate (500 ml) and 2-propanol (100 ml) in one lot and the solution cooled to 20-25° C. To the solution was added a solution of aqueous formic acid (70%) till turbidity develops at a pH of about 3.80. The mixture was seeded with crystals of ceftriaxone, stirred for 30-45 minutes. The pH was adjusted to 2.50 and cooled to 0-5° C. and agitated for 120 minutes. The crystallized solid was filtered.

The wet material was optionally redissolved in water with the aid of triethylamine and recrystallized as per the method outlined above to give ceftriaxone (I).

Step-5: Preparation of Ceftriaxone Sodium (II)

To water (600 ml) cooled to 0-5° C. was added the wet ceftriaxone obtained in Step-4. to the mixture was added triethylamine (36.42 gm; 0.360 moles) till a clear solution was obtained, maintaining a pH of 5.4±0.20. The solution was charcoalized and the charcoal filtered off. To the filtrate was added a mixture of water (100 ml) and acetone (100 ml), followed by addition of a solution of 2-ethyl sodium hexanoate (64.35 gm; 0.387 moles) in acetone (600 ml) over a period of 3-45 minutes at 0-5° C. Thereafter, the temperature was raised to 20±2° C. and the reaction mixture agitated at this temperature for 15-30 minutes. Acetone (1000 ml) was added till turbidity develops to the solution. Thereafter, further acetone (2500 ml) was added and the mixture agitated at 20±2° C. for 90-120 minutes. The mixture was cooled to 13-15° C., agitated for 60 minutes and the solid filtered, washed with acetone (400 ml) and dried under vacuum at 25° C. to give 97.88 gm (54.89%) of ceftriaxone sodium (II), possessing the following characteristics.

| Purity | 94.04% |
| Water Content | 9.45% |
| color absorbance | 0.046 AU |
| Total Impurities | 0.0.06% |

What is claimed is:

1. A process for the preparation of ceftriaxone sodium of formula (II),

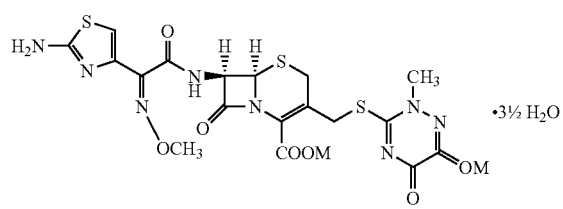

(II)

comprising the steps of
   i) reacting a silylated compound of formula (III),

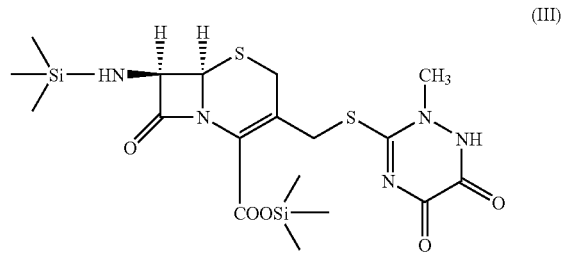

(III)

with a 4-halo-2-methoxyimino-3-oxo-butyric acid derivative of formula (IV),

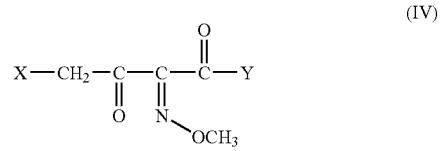

(IV)

wherein X and Y represent a halogen atom to give a compound of formula (V),

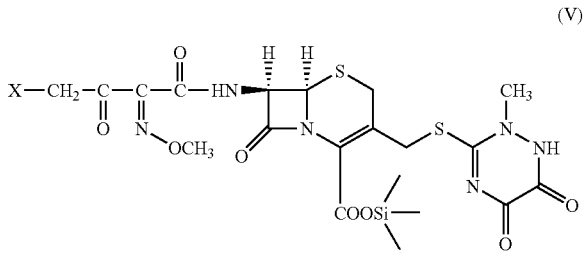

(V)

ii) desilylating the compound of formula (V), wherein X is as defined hereinabove to give the desilylated compound of formula (VI),

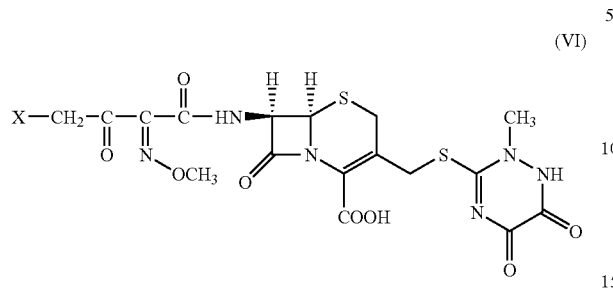

(VI)

iii) reacting the desilylated compound of formula (VI) with thiourea in a solvent system containing organic solvent and water, to obtain ceftriaxone of formula (I),

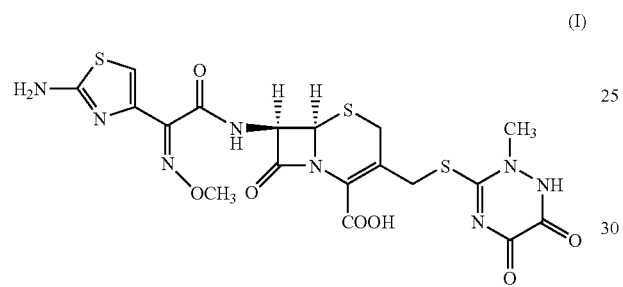

(I)

iv) converting the compound of formula (I) to the sodium salt (II); wherefore the improvement comprises i¹) reacting a silylated compound of formula (III),

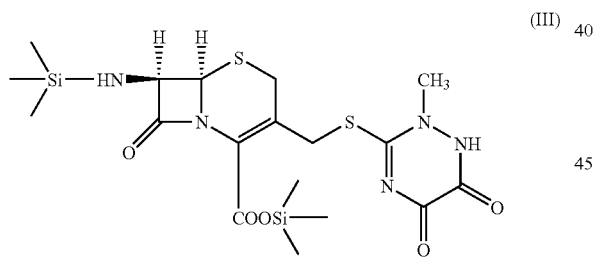

(III)

with a 4-halo-2-methoxyimino-3-oxo butyric acid derivative of formula (IV) having a purity of at least 95%, said 4-halo-methyloxyimino-3-oxo-butyric acid derivative containing 0.50% or less total di-brominated and poly-brominated impurity compounds,

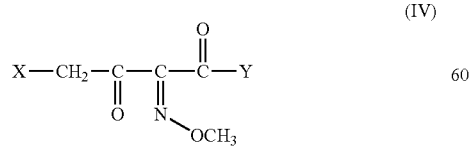

(IV)

wherein X represents Br and Y represents Cl, in the presence of an inert water-immiscible organic solvent or mixtures thereof and in the presence of an acid scavenging agent at a temperature of between −10° C. to −0° C. to give a compound of formula (V),

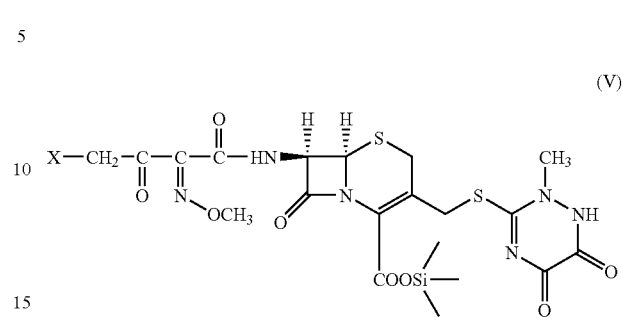

(V)

ii¹) adding the solution of compound of formula (V) in the inert water-immiscible organic solvent or mixtures thereof to a 1:1 mixture of water and a water-immiscible organic solvent and separation of the organic phase to provide a solution of compound of formula (VI) in the inert water-immiscible organic solvent or mixtures thereof,

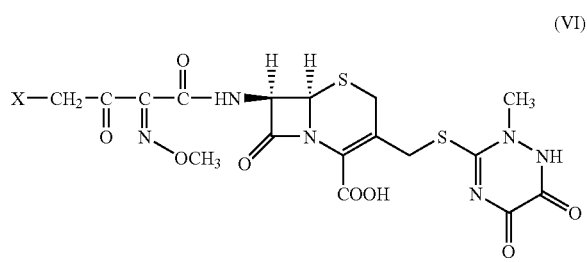

(VI)

iii¹) reacting the solution of compound of formula (VI) in the inert water-immiscible organic solvent admixed with a solution of thiourea in water, adding an alkali metal containing inorganic base at a temperature of between 0° C. to +10° C., maintaining the reaction mixture at a pH ranging between 5.0 to 5.5, and removing the organic layer to provide a solution of the alkali metal salt of ceftriaxone of formula (II¹) in water, wherein M is an alkali metal,

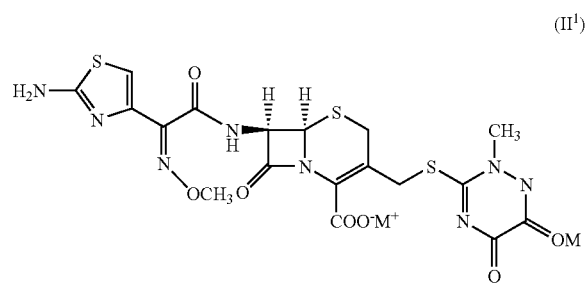

(II¹)

iv¹) mixing the solution of the alkali metal salt of ceftriaxone (II¹) in water with a water-immiscible organic solvent and a water-miscible solvent and treating the solution thus obtained with an acid to a pH of 3.6 to 4.0 and isolating the precipitated ceftriaxone of formula (I) by filtration, (I)

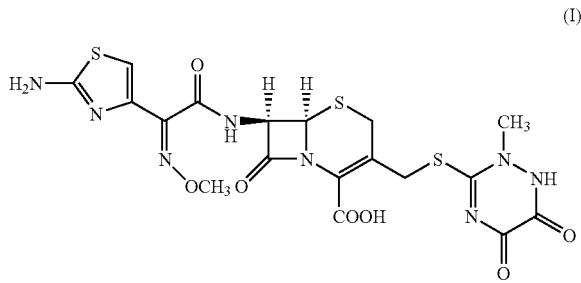

v¹) reacting solution of ceftriaxone of formula (I) in water with an organic amine maintaining a pH of 5.4±0.2 to produce a solution of the amine salt of ceftriaxone in water of formula (VII), (VII)

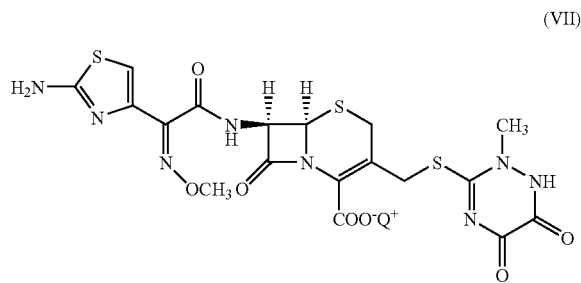

wherein Q⁺ represents the protonated organic amine, and (vi¹) reaction of the amine salt of ceftriaxone of formula (VII) in a mixture of water and a water-miscible organic solvent with a sodium ion carrier to give after crystallization ceftriaxone sodium of formula (II)

(II)

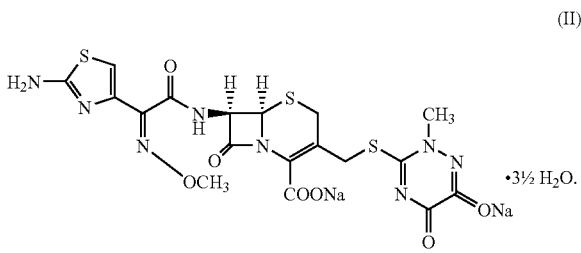

2. A process according to claim 1, in which in step i¹), the inert water-immiscible organic solvent is selected from the group consisting of chlorinated hydrocarbons, acetic acid ($C_{1-4}$) alkyl esters, and ethers.

3. A process according to claim 1, in which in step i¹), wherein the acid scavenging agent is selected from the group consisting of ethylene oxide, propylene oxide, butylene oxide, acetamide, epichlohydrin, calcium oxide, disodium hydrogen phosphate, calcium carbonate and quaternary ammonium phosphates.

4. A process according to any one of claims 1 and 2, wherein the acid scavenging agent is acetamide.

5. A process according to any one of claims 1, 2 and 3, wherein the acid scavenging agent is employed in molar proportions of 1.0 to 3.0 moles per mole of compound of formula (III).

6. A process according to any one of claims 1, 2, and 3 wherein the acid scavenging agent is employed in molar proportions of 1.0 to 1.5 moles per mole of compound of formula (III).

7. A process according to claim 1, in which in step ii¹), the water-miscible organic solvent is selected from the group consisting of tetrahydrofuran and acetonitrile.

8. A process according to claim 1, in which in step iii¹), thiourea is employed in molar proportions of 1.0 to 3.0 moles per mole of compound of formula (III), in molar proportions of 1.0 to 1.5 moles per mole of compound of formula (III).

9. A process according to claim 1, in which in step iii¹), the alkali metal inorganic base is selected from the group consisting of sodium hydroxide, potassium hydroxide, lithium hydroxide, sodium carbonate, potassium carbonate, lithium carbonate, sodium hydrogen carbonate, potassium hydrogen carbonate, and lithium hydrogen carbonate.

10. A process according to any one of claims 1 and 9, wherein the alkali metal containing inorganic base is employed in molar proportions of 2.0 to 5.0 moles per mole of compound of formula (III), in molar proportions of 2.0 to 3.0 moles per mole of compound of formula (III).

11. A process according to claim 1, in which in step iv¹), the water-immiscible organic solvent is selected from the group consisting of chlorinated hydrocarbons, acetic acid ($C_{1-4}$) alkyl esters, and ethers.

12. A process according to claim 1, in which in step iv¹), the water-miscible organic solvent is selected from the group consisting of tetrahydrofuran, acetonitrile or a ($C_{1-4}$) lower alcohol.

13. A process according to claim 1, in which in step v¹), the organic amine is selected from the group consisting of diethylamine, triethylamine, diisopropylamine, cyclohexylamine, pyridine, 2,4-dimethylamino pyridine, and N-methyl morpholine.

14. A process according to claim 1, in which in step vi¹), the water-miscible organic solvent is select d from the group consisting of tetrahydrofuran, acetonitrile, a $C_{1-4}$ lower alcohol, and a ketone.

15. A process according to claim 1. in which in step vi¹), the sodium ion carrier is selected from the group consisting of sodium acetate, 2-ethyl sodium hexanoate, and 2-ethyl sodium octanoate.

16. A process according to claim 1, wherein the ceftriaxone sodium of formula (II) has a color absorbance of 0.04 to 0.05 AU at 450 nm.

17. A process according to claim 1, wherein the level of total impurities in ceftriaxone sodium (II) obtained is in the range of between 0.05 to 0.20%.

18. A process for preparation of an alkali metal salt of ceftriaxone of formula (II¹) in water, wherein M is an alkali metal,

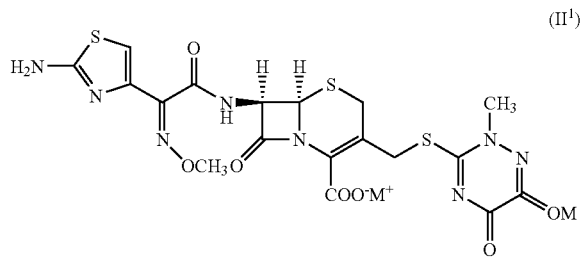

(II¹)

comprising the steps of:
i) reacting a silylated compound of formula III,

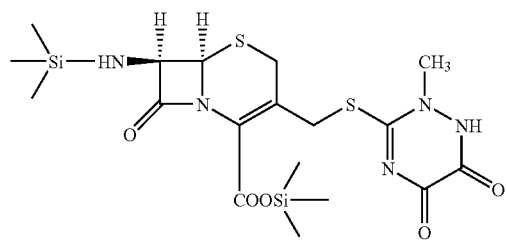

(III)

with a 4-halo-2-methoxyimino-3-oxo butyric acid derivative of formula (IV), said 4halo-methyloxyimino-3-oxo-butyric acid derivative having a purity of at least 95%, and said 4-halo-methyloxyimino-3-oxo-butyric acid derivative containing 0.50% or less total di-brominated and poly-brominated compounds,

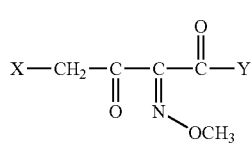

(IV)

wherein X and Y represent a halogen atom in the presence of an inert water-immiscible organic solvent or mixtures thereof and in the presence of an acid scavenging agent at a temperature of between −10° C. to −0° C. give a compound of formula (V),

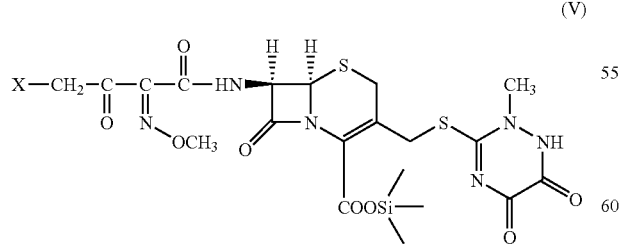

(V)

ii) adding the solution of compound of formula (V) in the inert water-immiscible organic solvent or mixtures thereof to a 1:1 mixture of water and a water-immiscible organic solvent and separation of the organic phase to provide a solution of compound of formula (VI) in the inert water-immiscible organic solvent or mixtures thereof,

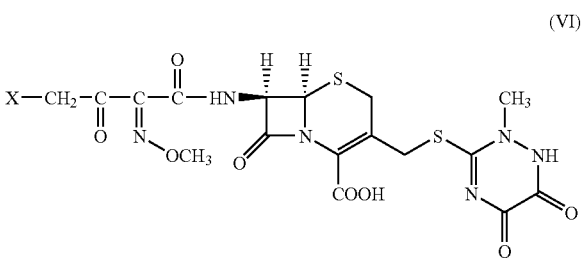

(VI)

iii) reacting the solution of compound of formula (VI) in the inert water-immiscible organic solvent or mixtures thereof with a solution of thiourea in water in the presence of an alkali metal containing inorganic base at a temperature of between 0° C. to +10° C. at a pH ranging between 5.0 to 5.5 and separation of the organic layer to provide a solution of the alkali metal salt of ceftriaxone of formula (II¹) in water, wherein M is an alkali metal,

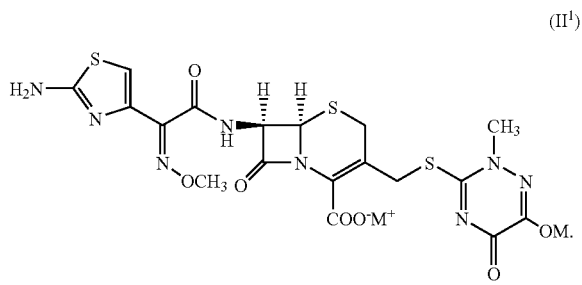

(II¹)

19. A process for the preparation ceftriaxone of formula (I) comprising the step of mixing a solution of a alkali metal salt of ceftriaxone of the formula (II¹), in water with a water-immiscible organic solvent and a water-miscible solvent and treating the solution thus obtained with an acid to a pH of 3.6 to 4.0 and isolating the precipitated ceftriaxone of formula (I)

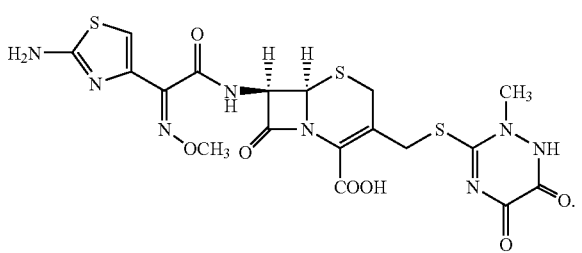

(I)

20. A process for the preparation a ceftriaxone of formula (VII) comprising the step of reacting a solution of ceftriaxone of formula (I) in water with an organic amine while maintaining a pH of 5.4+/−0.2 to produce a solution of the amine salt of ceftriaxone in water of formula (VII)

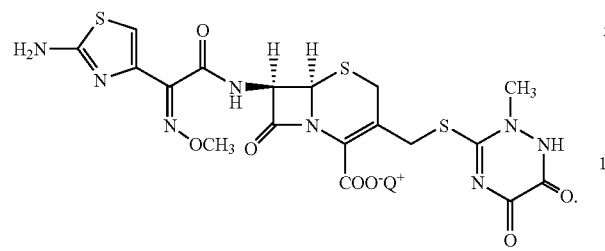

(VII)

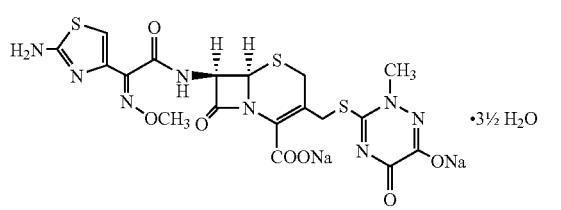

(II)

21. A process for the preparation ceftriaxone sodium of formula (II) comprising the step of reacting an amine salt of ceftriaxone of formula (VII) in a mixture of water and a water-miscible organic solvent with a sodium ion carrier to give ceftriaxone sodium of formula (II) after crystallization, containing 0.20% or less impurities and having a color absorbance of 0.05 AU or less at 450 nm.

* * * * *